(12) United States Patent
Lo et al.

(10) Patent No.: US 10,435,754 B2
(45) Date of Patent: *Oct. 8, 2019

(54) DIAGNOSTIC METHOD

(71) Applicant: The Chinese University of Hong Kong, Shatin (CN)

(72) Inventors: Yuk Ming Dennis Lo, Kowloon (CN); Kwan Chee Allen Chan, Mei Foo Sun Chuen (CN); Chunming Ding, Shatin (CN)

(73) Assignee: The Chinese University Of Hong Kong, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/162,258

(22) Filed: May 23, 2016

(65) Prior Publication Data

US 2017/0101685 A1    Apr. 13, 2017

Related U.S. Application Data

(63) Continuation of application No. 11/861,809, filed on Sep. 26, 2007, now Pat. No. 9,371,566.

(60) Provisional application No. 60/847,499, filed on Sep. 27, 2006.

(51) Int. Cl.
   *C12Q 1/6886*   (2018.01)

(52) U.S. Cl.
   CPC ...... *C12Q 1/6886* (2013.01); *C12Q 2600/118* (2013.01); *C12Q 2600/154* (2013.01)

(58) Field of Classification Search
   None
   See application file for complete search history.

(56) References Cited

U.S. PATENT DOCUMENTS

| | | | |
|---|---|---|---|
| 6,258,540 B1* | 7/2001 | Lo ................ | C12Q 1/6879 435/440 |
| 6,355,623 B2* | 3/2002 | Seidman ............ | A61K 31/52 514/263.4 |
| 6,596,488 B2 | 7/2003 | Pfeifer et al. | |
| 6,596,493 B1 | 7/2003 | Reeves et al. | |
| 6,630,301 B1 | 10/2003 | Gocke et al. | |
| 6,664,056 B2 | 12/2003 | Lo et al. | |
| 6,753,137 B2 | 6/2004 | Lo et al. | |
| 6,773,897 B2 | 8/2004 | Herman et al. | |
| 6,927,028 B2 | 8/2005 | Dennis et al. | |
| 7,022,478 B2 | 4/2006 | Rainer et al. | |
| 7,655,399 B2 | 2/2010 | Cantor et al. | |
| 7,700,282 B2 | 4/2010 | Tetzner et al. | |
| 7,700,324 B1 | 4/2010 | Issa et al. | |
| 7,727,720 B2 | 6/2010 | Dhallan | |
| 7,749,702 B2 | 7/2010 | Lofton-Day et al. | |
| 7,754,428 B2 | 7/2010 | Lo et al. | |
| 7,785,798 B2 | 8/2010 | Cantor et al. | |
| 7,899,626 B2 | 3/2011 | Kruglyak et al. | |
| 8,076,063 B2 | 12/2011 | Fan et al. | |
| 8,133,986 B2 | 3/2012 | Issa et al. | |
| 8,150,626 B2 | 4/2012 | Fan et al. | |
| 8,288,100 B2 | 10/2012 | Lo et al. | |
| 8,927,209 B2 | 1/2015 | Hamamoto et al. | |
| 8,927,216 B2 | 1/2015 | Lo et al. | |
| 9,121,069 B2 | 9/2015 | Lo et al. | |
| 9,371,566 B2* | 6/2016 | Lo ................ | C12Q 1/6886 |
| 9,732,390 B2 | 8/2017 | Lo et al. | |
| 2001/0051341 A1 | 12/2001 | Lo et al. | |
| 2002/0098530 A1 | 7/2002 | Pfeifer et al. | |
| 2003/0138783 A1 | 7/2003 | Sukumar et al. | |
| 2003/0228575 A1 | 12/2003 | Yeung et al. | |
| 2004/0005551 A1 | 1/2004 | Lo et al. | |
| 2004/0009518 A1 | 1/2004 | Lo et al. | |
| 2004/0038245 A1 | 2/2004 | Belinsky et al. | |
| 2004/0053304 A1 | 3/2004 | Markowitz et al. | |
| 2004/0086864 A1 | 5/2004 | Lo et al. | |
| 2004/0137474 A1 | 7/2004 | Levenson et al. | |
| 2004/0203037 A1 | 10/2004 | Lo et al. | |
| 2005/0026183 A1 | 2/2005 | Fan et al. | |
| 2005/0064410 A1 | 3/2005 | Distler et al. | |
| 2005/0112558 A1 | 5/2005 | Lo et al. | |

(Continued)

FOREIGN PATENT DOCUMENTS

CN    1451759 A  * 10/2003  .............. C12Q 1/25
JP    H06102036 B2    12/1994

(Continued)

OTHER PUBLICATIONS

Yeo et al. (Liver International Apr. 2005:25: 266-272) (Year: 2005).*

(Continued)

*Primary Examiner* — Peter J Reddig

(74) *Attorney, Agent, or Firm* — Wilson Sonsini Goodrich & Rosati

(57) ABSTRACT

The present invention concerns a method for the detection or monitoring of cancer using a biological sample selected from blood, plasma, serum, saliva, urine from an individual, said method comprising:

(a) obtaining DNA from the said biological sample;

(b) digesting the DNA sample with one or more methylation-sensitive restriction enzymes;

(c) quantifying or detecting a DNA sequence of interest after step (b), wherein the target sequence of interest contains at least two methylation-sensitive restriction enzyme recognition sites; and (d) comparing the level of the DNA sequence from the individual to a normal standard, to detect, prognosticate or monitor cancer.

20 Claims, 6 Drawing Sheets

Specification includes a Sequence Listing.

(56) References Cited

U.S. PATENT DOCUMENTS

| | | |
|---|---|---|
| 2005/0153316 A1 | 7/2005 | Jeddeloh et al. |
| 2005/0158731 A1 | 7/2005 | Plass et al. |
| 2005/0158739 A1 | 7/2005 | Jeddeloh et al. |
| 2005/0196792 A1 | 9/2005 | Fodor et al. |
| 2005/0282185 A1 | 12/2005 | Lo et al. |
| 2005/0287553 A1 | 12/2005 | Guetig et al. |
| 2006/0019278 A1 | 1/2006 | Lo et al. |
| 2006/0212461 A1 | 9/2006 | Meysman et al. |
| 2006/0252071 A1 | 11/2006 | Lo et al. |
| 2006/0252723 A1 | 11/2006 | MacLeod et al. |
| 2006/0292585 A1 | 12/2006 | Nautiyal et al. |
| 2007/0059753 A1* | 3/2007 | Vener .......... C12Q 1/6809 435/6.12 |
| 2007/0207466 A1 | 9/2007 | Cantor et al. |
| 2007/0243546 A1 | 10/2007 | Cao et al. |
| 2007/0275402 A1 | 11/2007 | Lo et al. |
| 2008/0081338 A1 | 4/2008 | Lo et al. |
| 2009/0117538 A1 | 5/2009 | Hashimoto et al. |
| 2009/0155776 A1* | 6/2009 | Lo .......... C12Q 1/6876 435/6.12 |
| 2011/0028333 A1 | 2/2011 | Christensen et al. |
| 2013/0079241 A1 | 3/2013 | Luo et al. |
| 2013/0084566 A1 | 4/2013 | Lo et al. |
| 2014/0080715 A1 | 3/2014 | Lo et al. |
| 2014/0272975 A1 | 9/2014 | Lo et al. |
| 2016/0017419 A1 | 1/2016 | Chiu et al. |
| 2017/0233829 A1 | 8/2017 | Lo et al. |
| 2017/0235877 A1 | 8/2017 | Lo et al. |

FOREIGN PATENT DOCUMENTS

| | | | |
|---|---|---|---|
| WO | WO-2005040399 A2 * | 5/2005 | .......... C12Q 1/683 |
| WO | WO-2005042704 A2 | 5/2005 | |
| WO | WO-2005054465 A1 | 6/2005 | |
| WO | WO-2005118852 A2 | 12/2005 | |
| WO | WO-2005123941 A1 | 12/2005 | |
| WO | WO-2007106802 A2 | 9/2007 | |
| WO | WO-2007132166 A2 | 11/2007 | |
| WO | WO-2008038000 A1 | 4/2008 | |
| WO | WO-2011038507 A1 | 4/2011 | |
| WO | WO-2011092592 A2 | 8/2011 | |
| WO | WO-2014043763 A1 | 3/2014 | |
| WO | WO2015054080 A1 | 4/2015 | |
| WO | WO-2016127944 A1 | 8/2016 | |

OTHER PUBLICATIONS

Chang et al. (Int. J. Caner 2003 105: 851-855) (Year: 2003).*
Wong et al. (Clinical Cancer Res. Apr. 1, 2004, 10: 2401-2406) (Year: 2004).*
Anacleto, et al. Development and application of a multiplex PCR procedure for the detection of DNA methylation in colorectal cancer. Oncol Rep 2005;13:325-8.
Banks, et al. Genetic and epigenetic analysis of von Hippel-Lindau (VHL) gene alterations and relationship with clinical variables in sporadic renal cancer. Cancer Res 2006;66:2000-11.
Barmann, et al. The prognostic impact of O6-Methylguanin-DNA Methyltransferase (MGMT) promoter hypermethylation in esophageal adenocarcinoma. Int J Cancer 2006;119:264-8.
"Bock, et al. Quantitative comparison of genome-wide DNA methylation mapping technologies. Nature Biotechnology, Oct. 2010, vol. 28, No. 10, p. 1106-1114".
Boltze, et al. Hypermethylation of the CDKN2/p16INK4A promoter in thyroid carcinogenesis. Pathol Res Pract 2003;199:399-404.
Bornman, et al. Methylation of the E-cadherin gene in bladder neoplasia and in normal urothelial epithelium from elderly individuals. Am J Pathol 2001;159:831-5.
Burbee DG, et al. Epigenetic inactivation of RASSF1A in lung and breast cancers and malignant phenotype suppression. J Natl Cancer Inst 2001;93:691-9.

Chan MW, et al. Frequent hypermethyaltion of promoter region of RASSF1A in tumor tissues and voided urine of urinary bladder cancer patients. Int J Cancer 2003;104:611-6.
Chen, et al. E-cadherin expression is silenced by DNA methylation in cervical cancer cell lines and tumours. Eur J Cancer 2003;39:517-30.
Chen, et al. Methylation of p16 and p15 genes in multiple myeloma. Chin Med Sci J 2003; 17:101-5.
Chen, et al. SOCS1 methylation in patients with newly diagnosed acute myeloid leukemia. Genes Chromosomes Cander 2003;37:300-5.
Choi N, et al. RASSF1A is not appropriate as an early detection marker or a prognostic marker for non-small cell lung cancer. Int J Cancer 2005;115:575-81.
"Damman R, et al. The CpG island of the novel tumor suppressor gene RASSF1A is intensely methylated in primary small cell lung carcinomas. Oncogene 2001;20:3536-7."
Dammann R, et al. Frequent RASSF1A promoter hypermethylation and K-ras mutations in pancreatic carcinoma. Oncogene 2003;22:3806-12.
Dansranjavin T, et al. E-cadherin and DAP kinase in pancreatic adenocarcinoma and corresponding lymph node metastases. Oncol Rep 2006;15:1125-31.
Dhillon VS, et al. The contribution of genetic and epigenetic changes in granulosa cell tumors of ovarian origin. Clin Cancer Res 2004;10:5537-45.
Dominguez, et al. Prevalance of aberrant methylation of p14ARF over p16INK4a in some human primary tumors. Mutat Res 2003;530:9-17.
Dulaimi E, et al. Promoter hypermethylation profile of kidney cancer. Clin cancer Res 2004;10:3972-9.
Dulaimi E, et al. Tumor suppressor gene promoter hypermethylation in serum of breast cancer patients. Clin Cancer Res 2004;10:6189-93.
Ekmekci, et al. Aberrant methylation of multiple tumor suppressor genes in acute myeloid leukemia. Am J Hematol 2004;77:233-40.
Esteller. Epigenetic lesions causing genetic lesions in human cancer: promoter hypermethylation of DNA repair genes. Eur J Cancer 2000;36:2294-300.
"Fackler, et al. Quantitative multiplex methylation-specific PCR assay for the detection of promoter hypermethylation in multiple genes in breast cancer. Cancer Res. Jul. 1, 2004; 64(13): 4442-4452. doi: 10.1158/0008-5472.CAN-03-3341".
Fackler MJ, et al. DNA methylation of RASSF1A, HIN-1, RAR-beta, Cyclin D2 and Twist in in situ and invasive lobular breast carcinoma. Int J Cancer 2003;107:970-5.
Fox, et al. Mutually exclusive promoter hypermethylation patterns of hMLH1 and O6-methylguanine DNA methyltransferase in colorectal cancer. J Mol Diagn 2006;8:68-75.
Fujitake, et al. Aberrant methylation of SOCS-1 was observed in younger colorectal cancer pateitns. J Gastroenterol 2004;39:120-4.
Fujiwara, et al. Identification of epigenetic aberrant promoter methylation in serum DNA is useful for early detection of lung cancer. Clin Cancer Res 2005;13:325-8.
Gifford, et al. The acquisition of hMLH1 methylation in plasma DNA after chemotherapy predicts poor survival for ovarian cancer patients. Clin Cancer Res 2004;10:4420-6.
"Grote HJ, et al. Methylation of RAS association domain family protein 1A as a biomarker of lung cancer. Cancer 2006;108:129-34."
Grover, et al. Tumor-associated endothelial cells display GSTP1 and RARbeta2 promoter methylation in human prostate cancer. J Transl Med 2006;4:13.
Gutierrez MI, et al. CpG island methylation in Schistosoma- and non-Schistosoma-associated bladder cancer. Mod Pathol 2004;17:1268-74.
Hesson, et al. CpG island promoter hypermethylation of a novel Ras-effector gene RASSF2A is an early event in colon carcinogenesis and correlates inversely with K-ras mutations. Oncogene 2005;24:3987-94.
Hesson, et al. NORE1A, a homologue of RASSF1A tumour suppressor gene is inactivated in human cancers. Oncogene 2003;22:947-54.

(56) References Cited

OTHER PUBLICATIONS

Hiltunen MO, et al. Hypermethylation of the APC (adenomatous polyposis coli) gene promoter region in huma colorectal carcinoma. Int J Cancer 1997;70-644-8.
Hiraguri, et al. Mechanisms of inactivation of E-cadherin in breast cancer cell lines. Cancer Res 1998;58:1972.7.
Hoque, et al. Quantitative methylation-specific polymerase chain reaction gene patterns in urine sediment distinguish prostate cancer patients from control subjects. J Clin Oncol 2005;23:6569-75.
Hsu, et al. Promoter hypermethylation is the predominant mechanism in hMLH1 and hMSH2 deregulation and is a poor prognostic factor in nonsmoking lung cancer. Clin Cancer Res 2005;11:5410-6.
Iida, et al. Alterations and hypermethylation of the p14(ARF) gene in gastric cancer. Int J Cancer 2000;87:654-8.
Ikoma, et al. Correlation between serum DNA methylation and prognosis in gastric cancer patients. Anticancer Res 2006;26:2313-6.
Irimia, et al. CpG island promoter hypermethylation of the Ras-effector gene NORE1A occurs in the context of a wild-type K-ras in lung cancer. Oncogene 2004;23:8695-9.
Ito, et al. Frequent inactivation of RASSF1A, BLU, and SEMA3B on 3p21.3 by promoter hypermethylation and allele loss in non-small cell lung cancer. Cancer Lett 2005;223:131-9.
"Jeronimo C, et al. A quantitative promoter methylation profile of prostate cancer. Clin Cancer Res 2004;10:8472-8."
Jin Z, et al. Adenomatous polyposis coli (APC) gene promoter hypermethylation in primary breast cancers. Br J Cancer 2001;85:69-73.
"Kang GH, et al. Aberrant CpG island hypermethylation of multiple genes in prostate cancer and prostatic intraepithelial neoplasia. J Pathol 2004;202:233-40."
Kawakami, et al. Multipoint methylation and expression analysis of tumor suppressor genes in human renal cancer cells. Urology 2003;61:226-30.
Kawakami K, et al. Hypermethylated APC DNA in plasma and prognosis of patients with esophageal adenocarcinoma. J Natl Cancer Inst 200;92:1805-11.
Komazaki, et al. Hypermethylation-associated inactivation of the SOCS-1 gene, a JAK/STAT inhibitor, in human pancreatic cancers. Jpn J clin Oncol 2004;34:191-4.
Kurakawa, et al. Hypermethylation of p16(INK4a) and p15(INK4b) genes in non-small cell lung cancer. Int J Oncol 2001;19:277-81.
Kwong, et al. Promoter hypermethylation of multiple gnes in nasopharyngeal carcinoma. Clin Cancer Res 2002;8:131-7.
Lee MG, et al. Frequent epigenetic inactivation of RASSF1A in human bladder carcinoma. Cancer Res 2001;61:6688-92.
Leung WK, et al. Potential diagnostic and prognostic values of detecting promoter hypermethylation in the serum of patients with gastric cancer. Br J Cancer 2005;92:2190-4.
Li, et al. Methylation of the E-cadherin gene promoter correlates with progression of prostate cancer. J Urol 2001;166:705.9.
Li, et al. Stud on the status of methylation of Rb gene promoter in human esophageal cancer and effect of NMBzA on Rb gene promoter in monkey esophageal epithelium. Zhonghua Zhong Liu Za Zhi 1998;20:412-4.
Lin, et al. Promoter CpG methylation of tumor suppressor genes in colorectal cancer and its relationship to clinical features. Oncol Rep 2004;11:341-8.
Liu, et al. Methylation and messenger RNA expression of p15INK4b but not p16INK4a are independent risk factors for ovarian cancer. Clin Cancer Res 2005;11:4968-76.
"Liu L, et al. Frequent hypermethylation of the RASSF1A gene in prostate cancer. Oncogene 2002;21:6835-40."
Lo, et al. Quantitative analysis of cell-free Epstein-Barr virus DNA in plasma of patients with nasopharyngeal carcinoma. Cancer Res 1999;59:1188-91.
Makarla PB, et al. Promoter hypermethylation profile of ovarian epithelial neoplasms, Clin Cancer Res 2005;11:5365-9.

"Marini A, et al. Epigenetic inactivation of tumor suppressor genes in serum of patients with cutaneous melanoma. J Invest Dermatol 2006;126:422-31."
Maruyama, et al. Aberrant promoter methylation profile of bladder cancer and its relationship to clinicopathological features. Cancer Res 2001;61:8659-63.
Mehrotra J, et al. Very high frequency of hypermethylated genes in breast cancer metastasis to the bone, brain, and lung. Clin Cancer Res 2004;10:3104-9.
Munot, et al. Pattern of expression of genes linked to epigenetic silencing in human breast cancer. Hum Pathol 2006;37:989-99.
"Office action dated Nov. 4, 2016 for U.S. Appl. No. 14/495,791".
Oshimo, et al. Epigenetic inactivation of SOCS-1 by CpG island hypermethylation in human gastric carcinoma. Int J Cancer 2004;112-1003-9.
"Spugnardi M., et al. Epigenetic inactivation of RAS association domain family protein 1 (RASSF1A) in malignant cutaneous melanoma. Cancer Res 2003;63:1639-43".
"Quackenbush, et al. Microarray data normalization and transformation. Nature Genetics Supplement. Dec. 2002. vol. 32, p. 496-501".
"Robinson, et al. Evaluation of affinity-based genome-wide DNA methylation data: Effects of CpG density, amplification bias, and copy number variation. Nov. 2, 2010, vol. 20, p. 1719-1729".
Safar AM, et al. Methylation profiling of archived non-small cell lung cancer: a promising prognostic system. Clin Cancer Res 2005;11:4400-5.
Sambrook, Molecular Cloning a Laboratory Manual, 3rd Edition. 2001.
Sarrio D, et al. Epigenetic and genetic alterations of APC and CDH1 genes in lobular breast cancer: relationsihps with abnormal E-cadherin and catenin expression and microsatellite instability. Int J Cancer 2003;106:208-15.
Sato, et al. Hypermethylation of the p14(ARF) gene in ulcerative colitis-associated colorectal carcinogenesis. Cancer Res 2002;62:1148-51.
Silva et al, British Journal of Cancer, 80:1262-1264, 1999.
Stirzaker C, et al. Extensive DNA methylation spanning the Rb promoter in retinoblastoma tumors. Cancer Res 1997;57:2229-37.
Sutherland, et al. Differential hypermethylation of SOCS genes in ovariant and breast carcinomas. Oncogene 2004;23:7726-33.
Tamura G. Alterations of tumor suppressor and tumor-related genes in the development and progression of gastric cancer. World J Gastroenterol 2006;12:192-8.
Tokinaga K, et al. Hypermethylation of the RASSF1A tumor suppressor gene in Japanese clear cell renal cell carcinoma. Oncol Rep 2004;12:805-10.
Tong, et al. Quantitative Epstein-Barr virus DNA analysis and detection of gene promoter hypermethylation in nasopharyngeal (NP) brushing samples from patients with NP carcinoma, Clin Cancer Res 2002;8:2612-9.
Toyooka S, et al. Smoke exposure, histologic type and geography-related differences in the methylation profiles of non-small cell lung cancer. Int J Cancer 2003;103:153-60.
Tzao, et al. Promoter methylation of the hMLH1 gene and protein expression of human mutL homolog 1 and human mutS homolog 2 in resected esophageal squamous cell carcinoma. J Thorac Cardiovasc Surg 2005;130:1371.
Van Engeland M, et al. K-ras mutations and RASSF1A promoter methylation in colorectal cancer. Oncogene 2003;21:3792-5.
Virmani, et al. Aberrant methylation during cervical carcinogenesis. Clin Cancer Res 2001;7:584-9.
Wagner KJ, et al. Frequent RASSF!A tumour suppressor gene promoter methylation in Wilms' tumour and colorectal cancer. Oncogene 2002;21:7277-82.
Wenming, et al. Inactiavtion of p16 gene in leukemia. Chin Med Sci J 1999;14:206-10.
Yu, et al. Methylation profiling of twenty promoter-CpG islands of genes which may contribute to hepatocellular carcinogenesis. BMC Cancer 2002;2:29.
Xu XL, et al. Methylation profile of the promoter CpG islands of 31 genes that may contribute to colorectal carcinogenesis. World J Gastroenterol 2004;10:3441-54.

(56) References Cited

OTHER PUBLICATIONS

Yang, et al. Aberrant promoter methylation profiles of humor suppressor genes in hepatocellular carcinoma. Am J Pathol 2003;163:1101-7.
Yang HJ, et al. Detection of hypermethylated genes in tumor and plasma of cervical cancer patients, Gynecol Oncol 2004;93;435-40.
Ye, Relationship between tumor suppressor gene p16 and Rb and early diagnosis of lung cancers. Zhonghua Wai Ke Za Zhi 2000;38:537-41, 30.
Yegnasubramanian et al, Nucleic Acids Research, vol. 34, No. 3, 2006 e19.
Yenasubramanian S, et al. Hypermethylation of CpG islands in primary and metastatic human prostate cancer. Cancer Res 2004;64:1975-86.
"Yeo, et al. High frequency of promoter hypermethylation of RASSF1A in tumorous and non-tumorous tissue of breast cancer. Pathology 2005;37:125-30."
Yeo W, et al. High frequency of promoter hypermethylation of RASSF1A in tumor and plasma of patients in hepatocellular carcinoma. Liver Int 2005;25:266-72.
Yoon JH, et al. Hypermethylation of the CpG island of the RASSF1A gene in ovarian and renal cell carcinomas. Int J Cancer 2001;94:212-7.
Yoshikawa, et al. SOCS-1, a negative regulator of the JAK/STAT pathway, is silenced by methylation in human hepatocellular carcinoma and shows growth suppression-activity. Nat Genet 2001;28:29-35.
"Yu, et al. Tet-assisted bisulfite sequencing of 5-hydroxymethylcytosine. Nat Protoc. Dec 2012; 7(12): 2159-2170. Published online Nov. 29, 2012. doi: 10.1038/nprot.2012.137".
"Zhai, et al. Genome-wide DNA Methylation Profiling of Cell-Free Serum DNA in Esophageal Adenocarcinoma and Barrett Esophagus. Neoplasia. Jan. 2012; 14(1): 29-33."
Zhong S, et al. Intensive hypermethylation of the CpG island of Ras association domain family 1A in hepatitis B virus-associated hepatocellular carinomas. Clin Cancer Res 2003;9:3376-82.
Zochbauer, et al. Aberrant promoter methylation of multiple genes in non-small cell lung cancers. Cancer Res 2001;61:249-55.
Schagdarsurengin U, et al. Frequent epigenetic inactivation of the RASSF1A gene in hepatocellular carinoma, Oncogene 2003;22:1866-71.
2014 Procedure for Subject Matter Eligibility Analysis of Claims Reciting or Involving Laws of Nature/Natural Principles, Natural Phenomena, and/or Natural Products, Mar. 2014.
International Preliminary Report on Patentability, received in PCT Application No. PCT/GB2007/003674, dated Mar. 31, 2009.
International Search Report, received in PCT International Application No. PCT/GB2007/003674, dated Nov. 28, 2007.
Macmillan Dictionary, Kit, http://www.macmillandictionary.com/dictionary/american/kit, retrieved Aug. 23, 2013.
Stratagene Catalog (1988, p. 39).
Taber's Cyclopedic Medical Dictionary (1985, FA Davis Company, Philadelphia, p. 274).
Written Opinion, received in PCT International Application No. PCT/GB2007/003674, Dec. 7, 2007.

Bastian, PJ et al. Preoperative Serum DNA GSTP1 CpG Island Hypermethyfation and the Risk of Early Prostate-Specific Antigen Recurrence Following Radical Prostatectomy, Clinical Cancer Res. 11(11):4037-4043 (Jun. 1, 2005).
Buck, GA et al. Design Strategies and Performance of Custom DNA Sequencing Primers. Biotechniques 27(3):528-536 (1999).
Busken, et al. Digestive Disease Week Abstracts and Itinerary Planner, Abstract No. 850, 2003.
Capizzi, Principles of treatment of cancer, Internal Medicine. Jay Stein, 1994, 707-29.
Fukasawa, M. et al. Microarray Analysis of Promoter Methylation in Lung Cancers. Journal of Hum. Genet. 51 (4):368-374 (Jan. 25, 2006).
Hoque, et al. Detection of Aberrant Methylation of Four Genes in Plasma DNA for the Detection of Breast Cancer. Journal of Clinical Oncology, 24(26):4262-4269 (Sep. 10, 2006) E-Published Aug. 14, 2006.
Hoque, et al. Quantitation of Promoter Methylation of Multiple Genes in Urine DNA and Bladder Cancer Detection. J. Natl. Cancer Inst. 98(14); 996-1004 (Jul. 19, 2006).
Kaiser, Cancer. First pass at cancer genome reveals complex landscape, Science 313(5792); 1370 (2006).
Krontiris, et al. Molecular and cellular biology of cancer. Internal Medicine, 4th Edition, Editor-in-chief Jay Stein, Elsevier Science, Chapters 71-72, 1994, pp. 699-729.
Loginov, et al. Methylation of the Promoter Region of the RASSF1A Candidate Tumor Suppressor Gene in Primary Epithelial Tumors. Mol. Biol. 38;549-560 (Jul. 2004).
Maat, W. et al. Epigenetic Inactivation of RASSF1a in Uveal Melanoma. Invest. Ophthal. Vis. Sci. 48(2):486-490 (Feb. 2007).
Mensink, E. et al. Quantitation of minimal residual disease in Philadelphia chromosome positive chronic myeloid leukaemia patients using real-time quantitative RT-PCR. British J. Haematol. 102(3):768-774 (Aug. 1998).
Nutiu, R. et al. Fluorescence-Signaling Nucleic Acid-Based Sensors Madame Curie Bioscience Database [Internet]. Austin (TX): Landes Bioscience, 2000, 27 pages [https://www.ncbi.nlm.nih.gov/books/NBK5967/].
Peng, et al. The Methylation of p16 and RASSF1A Gene in Thyroid Carcinoma, Database EBML Accession No. DQ444319, Apr. 3, 2006.
Pritzker, Kenneth P.H. Cancer biomarkers: easier said than done. Clinical Chemistry, 48(8):1147-1150 (2002).
Xiong, Z. et al. COBRA: A Sensitive and Quantitative DNA Methylation Assay. Nucleic Acids Res. 25(12):2532-2534 (Jun. 1997).
Toyota, M. et al. Identification of differentially methylated sequences in colorectal cancer by methylated CpG island amplification. Cancer Research, 50(10); 2307-2312 (May 1999).
Ross, JP et al. Identification of differentially methylated regions usign streptavidin bisulfite ligand methylation enrichment (SuBLiME), a new method to enrich for methylated DNA prior to deep bisulfite genomic sequencing. Epigenetics, 8(1):113-127 (Jan. 2013) E-pub: Dec. 20, 2012.

* cited by examiner

Figure 6 cctagatcccagaaatctgggagcggctggagcgagaaaacagaggcaag
tggcaggcaattgccaagcaccagctccagcatgtgttcagcccctcaga
gcaggacctgcggctgcaggcgcgaaggtaaggcctgtggaaatggcagg
gagggtggaggggatgcaggaggcatggatgtgggtggggtgccccacc
ttccagggccagtcagaccttcctgactttcccccaggtgggctgagacc
tacaggctggatgtgctagaggcagtggctccagagcggcccgctgtgc
ttactgcagtgcagaggcttctaagcgctgctcacgatgccagaatgagt
ggtattgctgcaggtgagggtatcctagaaccttggacctctaagcccta
ctcccacatcccccacatgcattgccatcctcaatacccacctgcctgca
gggagtgccaagtcaagcactgggaaaagcatggaaagacttgtgtcctg
gcagcccagggtgacagagccaaatgagggctgcagttgctgagggccga
ccacccatgccaagggaatccacccagaatgcacccctgaacctcaagat
cacggtccagcctctgccggagcccagtctccgcagtggagagcagagc
gggcggtaaagctgctgaccgatctcctcctcctcaccccaagtgaagg
ctcgagacttcctgcccacccagtgggtaggccaagtgtgttgcttcag
caaaccggaccaggagggccagggccggatgtggggaccctcttcctcta
gcacagtaaagctggcctccagaaacacgggtatctcgcgtggtgcttt
gcggtcgccgtcgttgtggccgtccggggtggggtgtgaggaggggacga
aggagggaaggaagggcaaggcgggggggctctgcgagagcgcgcccag
ccccgccttcgggcccacagtccctgcaccaggtttccattgcgcggc
TCTCCTCAGCTCCTTCCCGCCGCCCAGTCTGGATCCTGGGGGAGGCGCTG
AAGTCGGGGCCCGCCCTGTGGCCCCGCCCGGCCCGCGCTTGCTAGCGCCC
AAAGCCAGCGAAGCACGGGCCCAACCGGGCCATGTCGGGGGAGCCTGAGC
TCATTGAGCTGCGGGAGCTGGCACCCGCTGGGCGCGCTGGGAAGGGCCGC
ACCCGGCTGGAGCGTGCCAACGCGCTGCGCATCGCGCGGGGCACCGCGTG
CAACCCCACACGGCAGCTGGTCCCTGGCCGTGGCCACCGCTTCCAGCCCG
CGGGGCCCGCCACGCACACGTGGTGCGACCTCTGTGGCGACTTCATCTGG
GGCGTCGTGCGCAAAGGCCTGCAGTGCGCGC

DIAGNOSTIC METHOD

CROSS REFERENCE TO RELATED PATENT APPLICATION

This application is a continuation of U.S. application Ser. No. 11/861,809, filed Sep. 26, 2007, issued as U.S. Pat. No. 9,371,566, which claims the benefit of the filing date of U.S. provisional patent application No. 60/847,499, filed Sep. 27, 2006, the disclosures of which are herein incorporated by reference.

FIELD OF THE INVENTION

The present invention relates to methods for diagnosis, prognosis or monitoring of cancer in an individual, in particular using the differential methylation patterns in genes associated with cancers.

BACKGROUND TO THE INVENTION

It is well known that many tumor suppressor genes are methylated in tumor cells. As such, the use of methylation markers has been suggested for the detection or monitoring of cancer in patients. A number of different methods have been proposed for detection of these methylated sequences.

Methylation specific PCR (MSP) is the most commonly used method for detecting methylated or unmethylated DNA. MSP involves the step of bisulfite conversion. Sodium bisulfite is used to deaminate cytosine to uracil while leaving 5-methyl-cytosine intact. Methylation-specific PCR uses PCR primers targeting the bisulfite induced sequence changes to specifically amplify either methylated or unmethylated alleles. Bisulfite conversion destroys about 95% of the DNA. Since DNA concentrations are typically very low in the serum or plasma, a 95% reduction in DNA results in a detection rate of less than 50%.

Alternative methods use restriction enzymes that digest specifically either the methylated or unmethylated DNA. Enzymes that cut specifically methylated DNA are rare. However, enzymes that cut specifically unmethylated DNA are more readily available. Detection methods then establish whether digestion has occurred or not, and thus depending on the specificity of the enzyme used, allows detection of whether the underlying DNA was methylated or unmethylated and thus associated with cancer or not.

Methylation-sensitive enzyme digestion has been previously proposed. For example, Silva et al, British Journal of Cancer, 80:1262-1264, 1999 conducted methylation-sensitive enzyme digestion followed by PCR. However, as noted by the authors Yegnasubramanian et al, Nucleic Acids Research, Vol. 34, No. 3, 2006 e19, such methods are plagued by the number of false-positives that are generated.

The present invention seeks to provide enhanced methods of methylation-sensitive detection which eliminate or reduce false positives and/or false negatives.

SUMMARY OF THE INVENTION

In accordance with the present invention, there is provided a method for the detection or monitoring of cancer using a biological sample selected from blood, plasma, serum, saliva, urine from an individual, said method comprising:
(a) obtaining DNA from the said biological sample;
(b) digesting the DNA sample with one or more methylation-sensitive restriction enzymes;
(c) quantifying or detecting a DNA sequence of interest after step (b), wherein the target sequence of interest contains at least two methylation-sensitive restriction enzyme recognition sites; and
(d) comparing the level of the DNA sequence from the individual to a normal standard, to detect, prognosticate or monitor cancer.

In a preferred aspect of the present invention, the polymerase chain reaction is used in step (c). Preferably, the methylation-sensitive restriction enzyme recognises DNA sequences which have not been methylated. The target sequence is a sequence susceptible to methylation in cancer patients so that an unmethylated target sequence in a normal patient is digested and is not amplified by the polymerase chain reaction, whereas in a cancer patient, the target sequence is methylated and is not digested by the enzyme and can subsequently be quantified or detected, for example using the polymerase chain reaction.

The methods of the present invention can be used to predict the susceptibility to cancer of the individual, to assess the stage of cancer in the individual, to predict the likelihood of overall survival for the individual, to predict the likelihood of recurrence for the individual or to assess the effectiveness of treatment in the individual.

In accordance with another aspect of the present invention, there is provided a method for the detection or monitoring of cancer using a biological sample selected from blood, plasma, serum, saliva, urine from an individual, said method comprising:
(a) obtaining DNA from the said biological sample;
(b) digesting the DNA sample with one or more methylation-sensitive restriction enzymes;
(c) quantifying or detecting a DNA sequence of interest after step (b) wherein the DNA sequence is a sequence comprising part or all of RASSF1A; and
(d) comparing the level of the DNA sequence from the individual to a normal standard, to detect, prognosticate or monitor cancer.

In accordance with a further aspect of the invention, there is provided probes, primers and kits for use in the method of the invention. In particular, there is provided:

a detectably-labelled probe for the detection or monitoring of cancer in a biological sample selected from blood, plasma, serum, saliva, urine from an individual, which comprises the sequence shown in SEQ ID NO: 4;

a set of primers for the detection or monitoring of cancer in a biological sample selected from blood, plasma, serum, saliva, urine from an individual, which comprises a primer comprising the sequence shown in SEQ ID NO: 2 and a primer comprising the sequence shown in SEQ ID NO: 3;

a kit for the detection or monitoring of cancer in a biological sample selected from blood, plasma, serum, saliva, urine from an individual, which comprises the probe of the invention and the set of primers of the invention a detectably-labelled probe for use as a control during the detection or monitoring of cancer in a biological sample selected from blood, plasma, serum, saliva, urine from an individual, which comprises the sequence shown in SEQ ID NO: 7;

a set of primers for use as a control during the detection or monitoring of cancer in a biological sample selected from blood, plasma, serum, saliva, urine from an individual, which comprises a primer comprising the sequence shown in SEQ ID NO: 5 and a primer comprising the sequence shown in SEQ ID NO: 6; and a kit for use as a control during the detection or monitoring of cancer in a biological sample selected from blood, plasma, serum, saliva, urine from an individual, which comprises the control probe of the invention and the set of control primers of the invention.

DESCRIPTION OF THE FIGURES

FIG. 6: Genomic sequence of the promoter and the first exon of the RASSF1A gene (SEQ ID NO: 1). The recognition sequence of the methylation-sensitive restriction enzyme BstUI is underlined and the target sequence for PCR detection is highlighted in bold. There are 5 BstUI enzyme restriction sites in the target sequence.

DETAILED DESCRIPTION OF THE INVENTION

Figure 1:
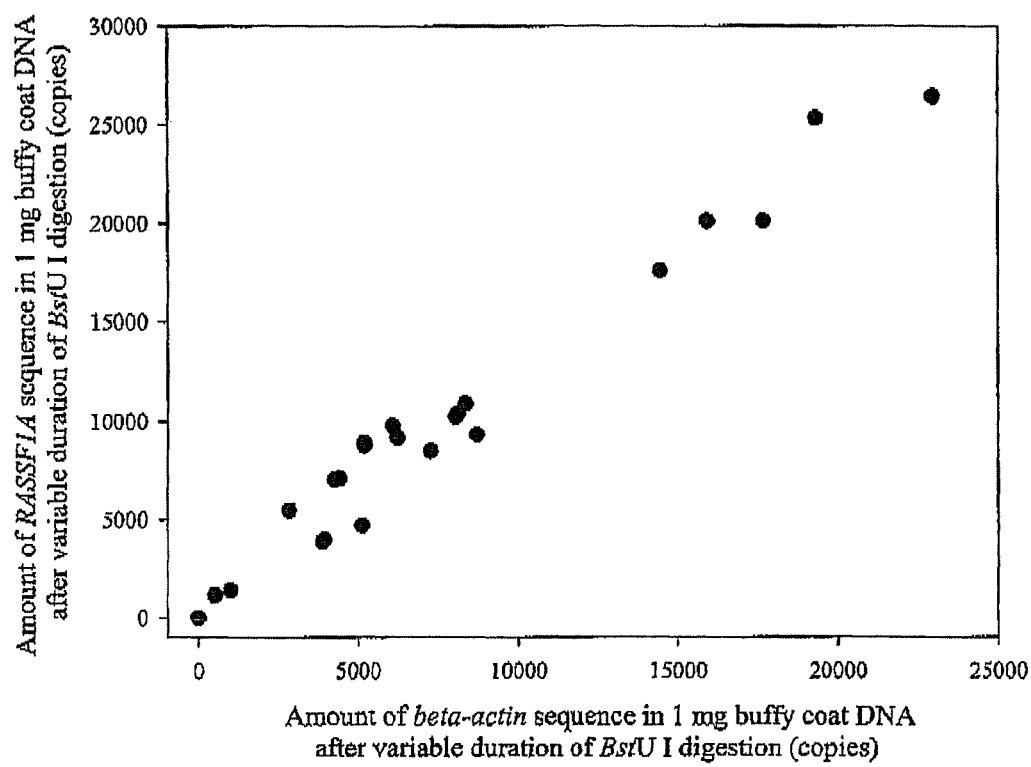
FIG. 1: concentration of methylated RASSF1A in patients' plasma.

The present invention provides a method to assess, diagnose, prognosticate or monitor the presence or progression of tumors in an individual. The method involves the use of a methylation-sensitive restriction enzyme to digest DNA sequences. DNA sequences of interest are selected which contain at least two restriction sites which may or may not be methylated. The method is preferably carried out with methylation-sensitive restriction enzymes which preferentially cleave unmethylated sequences compared to methylated sequences. Methylated sequences remain undigested and are detected. Digestion of unmethylated sequences at at least one of the methylation-sensitive restriction enzyme sites results in the target sequence not being detected or amplifiable. Thus a methylated sequence can be distinguished from an unmethylated sequence. In one embodiment of the invention, the quantity of uncut target sequence detected in a biological sample, e.g. plasma or serum of cancer patients is higher than that demonstrated in a biological sample of the same type of healthy or cancer-free individuals since the target sequences are more highly methylated in cancer patients than healthy individuals.

In the alternative, restriction enzymes which cut methylated DNA can be used. Unmethylated DNA sequences are not digested and can be detected. In another embodiment of this invention, lower quantifies of the uncut DNA sequence are detected in a biological sample, e.g. plasma, or serum of cancer patients when compared with that demonstrated in a biological sample of the same type in cancer-free individuals.

In a preferred embodiment according to the present invention, the target sequence is detected by amplification by PCR. Real-time quantitative PCR can be used. Primer sequences are selected such that at least two methylation-sensitive restriction enzyme sites are present in the sequence to be amplified using such primers. The methods in accordance with the present invention do not use sodium bisulfite. Amplification by a suitable method, such as PCR, is used to detect uncut target sequence, and thus to identify the presence of methylated DNA which has not been cut by restriction enzymes.

In accordance with the present invention, any suitable methylation-sensitive restriction enzyme can be used. Examples of methylation-sensitive restriction enzymes that cut unmethylated DNA are listed in Table I below.

TABLE I

Examples of methylation-sensitive restriction enzymes:

| Enzyme | Recognition sequence | Effect of CpG methylation on enzyme restriction* |
|---|---|---|
| AatII | GACGTC | blocked |
| AjiI | CACGTC | blocked |
| BstUI, Bsh1236I | CGCG | blocked |
| Bsh1285I | CGRYCG | blocked |
| BshTI | ACCGGT | blocked |
| Bsp68I | TCGCGA | blocked |
| Bsp119I | TTCGAA | blocked |
| Bsp143II | RGCGCY | blocked |
| Bsu15I | ATCGAT | blocked |
| CseI | GACGC | blocked |
| Cfr10I | RCCGGY | blocked |
| Cfr42I | CCGCGG | blocked |
| CpoI | CGGWCCG | blocked |
| Eco47III | AGCGCT | blocked |
| Eco52I | CGGCCG | blocked |
| Eco72I | CACGTG | blocked |
| Eco105I | TACGTA | blocked |
| EheI | GGCGCC | blocked |
| Esp3I | CGTCTC | blocked |
| FspAI | RTGCGCAY | blocked |
| HhaI; Hin6I | GCGC | blocked |
| Hin1I | GRCGYC | blocked |
| HpaII | CCGG | blocked |
| Kpn2I | TCCGGA | blocked |
| MluI | ACGCGT | blocked |
| NotI | GCGGCCGC | blocked |
| NsbI | TGCGCA | blocked |
| PauI | GCGCGC | blocked |
| PdiI | GCCGGC | blocked |
| Pl12311 | CGTACG | blocked |
| Pfl23II | CGTACG | blocked |
| Ppu21I | YACGTR | blocked |

TABLE I-continued

Examples of methylation-sensitive restriction enzymes:

| Enzyme | Recognition sequence | Effect of CpG methylation on enzyme restriction* |
|---|---|---|
| Psp1406I | AACGTT | blocked |
| PvuI | CGATCG | blocked |
| SalI | GTCGAC | blocked |
| SgsI | GGCGCGCC | blocked |
| SmaI | CCCGGG | blocked |
| SmuI | CCCGC | blocked |
| SsiI | CCGC | blocked |
| TaiI | ACGT | blocked |
| TauI | GCSGC | blocked |

The letter codes in the recognition sequences represent different combinations of nucleotides and are summarised as follows: R = G or A; Y = C or T; W = A or T; M = A or C; K = G or T; S = C or G; H = A, C or T; V = A, C or G; B = C, G or T; D = A, G or T; N = G, A, T or C.
The CpG dinucleotide(s) in each recognition sequence is/are underlined. The cytosine residues of these CpG dinucleotides are subjected to methylation.
*The methylation of the cytosine of the CpG dinucleotides in the recognition sequence would prevent enzyme cutting of the target sequence.

The target sequence includes two or more methylation-sensitive restriction enzyme sites. Such sites may be recognised by the same or different enzymes. However, the sites are selected so that at least two sites in each sequence are digested when unmethylated when using enzymes which preferentially cleave unmethylated sequences compared to methylated sequences.

In a less preferred embodiment the target sequence contains at least two sites which are cut or cleaved by restriction enzymes which preferentially cleave methylated sequences. The two or more sites may be cleaved by the same or different enzymes.

Any suitable DNA methylation marker may be used in accordance with the present invention. Such DNA methylation markers are those where the selected sequence shows a different methylation pattern in cancer patients compared to normal individuals. Suitable markers are selected such that the sequence to be amplified contains at least two methylation-sensitive restriction enzyme sites. Generally such methylation markers are genes where promoter and/or encoding sequences are methylated in cancer patients. Preferably the selected sequences are not methylated or are methylated to a lesser extent in non-cancer or cancer-free individuals.

Suitable DNA methylation markers include, for example, RASSF1A. Indeed, RASSF1A has proved to be particularly effective for use in detection or monitoring of cancer in an individual. Thus, in accordance with an alternative aspect of the present invention, there is provided a method for the detection or monitoring of cancer using a biological sample selected from blood, plasma, serum, saliva, urine from an individual, said method comprising:

(a) obtaining DNA from the said biological sample;
(b) digesting the DNA sample with one or more methylation-sensitive restriction enzymes;
(c) quantifying or detecting a DNA sequence of interest after step (b) wherein the DNA sequence is a sequence comprising part or all of RASSF1A; and
(d) comparing the level of the DNA sequence from the individual to a normal standard, to detect, prognosticate or monitor cancer.

The tumor types associated with RASSF1A promoter hypermethylation are listed in Table II below.

TABLE II

Frequencies of RASSF1A promoter hypermethylation in different types of cancers (ordered in descending frequency):

| Cancer types | Frequencies of RASSF1A promoter hypermethylation | References |
|---|---|---|
| Liver | 93%-100% | (1-4) |
| Breast | 49%-95% | (5-8) |
| Lung (small cell) | 79%-88% | (9, 10) |
| Prostate | 71%-83% | (11-13) |
| Melanoma | 41%-75% | (14, 15) |
| Pancreas | 64% | (16) |
| Kidney | 36%-64% | (17-19) |
| Bladder | 47%-60% | (20, 21) |
| Colon | 12%-45% | (19, 22-24) |
| Ovary | 30%-40% | (19, 25, 26) |
| Lung (non-small cell) | 28%-40% | (9, 27, 28) |

REFERENCES FOR TABLE II

1. Schagdarsurengin U, Wilkens L, Steinemann D, Flemming P, Kreipe H H, Pfeifer G P, et al, Frequent epigenetic inactivation of the RASSF1A gene in hepatocellular carcinoma. Oncogene 2003; 22:1866-71.
2. Zhong S, Yeo W, Tang M W, Wong N, Lai P B, Johnson P J. Intensive hypermethylation of the CpG island of Ras association domain family 1A in hepatitis B virus-associated hepatocellular carcinomas. Clin Cancer Res 2003; 9:3376-82.
3. Yeo W, Wong N, Wong W L, Lai P B, Zhong S, Johnson P J. High frequency of promoter hypermethylation of RASSF1A in tumor and plasma of patients with hepatocellular carcinoma. Liver Int 2005; 25:266-72.
4. Yu J, Ni M, Xu J, Zhang H, Gao B, Gu J, et al. Methylation profiling of twenty promoter-CpG islands of genes which may contribute to hepatocellular carcinogenesis. BMC Cancer 2002; 2:29.
5. Burbee D G, Forgacs E, Zochbauer-Muller S, Shivakumar L, Fong K, Gao B, et al. Epigenetic inactivation of RASSF1A in lung and breast cancers and malignant phenotype suppression. J Natl Cancer Inst 2001; 93:691-9.
6. Mehrotra J, Vali M, McVeigh M, Kaminsky S L, Fackler M J, Lahti-Domenici J, et al. Very high frequency of hypermethylated genes in breast cancer metastasis to the bone, brain, and lung. Clin Cancer Res 2004; 10:3104-9.
7. Fackler M J, McVeigh M, Evron E, Garrett E, Mehrotra J, Polyak K, et al. DNA methylation of RASSF1A, HIN-1, RAR-beta, Cyclin D2 and Twist in in situ and invasive lobular breast carcinoma. Int J Cancer 2003; 107:970-5.
8. Yeo W, Wong W L, Wong N, Law B K, Tse G M, Zhong S. High frequency of promoter hypermethylation of RASSF1A in tumorous and non-tumourous tissue of breast cancer. Pathology 2005; 37:125-30.
9. Grote H J, Schmiemann V, Geddert H, Bocking A, Kappes R, Gabbert H E, et al. Methylation of RAS association domain family protein 1A as a biomarker of lung cancer. Cancer 2006; 108:129-34.

10. Dammann R, Takahashi T, Pfeifer G P. The CpG island of the novel tumor suppressor gene RASSF1A is intensely methylated in primary small cell lung carcinomas. Oncogene 2001; 20:3563-7.
11. Jeronimo C, Henrique R, Hoque M O, Mambo E, Ribeiro F R, Varzim G, et al. A quantitative promoter methylation profile of prostate cancer. Clin Cancer Res 2004; 10:8472-8.
12. Kang G H, Lee S, Lee H J, Hwang K S. Aberrant CpG island hypermethylation of multiple genes in prostate cancer and prostatic intraepithelial neoplasia. J Pathol 2004; 202:233-40.
13. Liu L, Yoon J H, Dammann R, Pfeifer G P. Frequent hypermethylation of the RASSF1A gene in prostate cancer. Oncogene 2002; 21:6835-40.
14. Spugnardi M, Tommasi S, Dammam R, Pfeifer G P, Hoon D S. Epigenetic inactivation of RAS association domain family protein 1 (RASSF1A) in malignant cutaneous melanoma. Cancer Res 2003; 63:1639-43.
15. Marini A, Mirmohammadsadegh A, Nambiar S, Gustrau A, Ruzicka T, Hengge U R. Epigenetic inactivation of tumor suppressor genes in serum of patients with cutaneous melanoma. J Invest Dermatol 2006; 126:422-31.
16. Dammann R, Schagdarsurengin U, Liu L, Otto N, Gimm O, Dralle H, et al. Frequent RASSF1A promoter hypermethylation and K-ras mutations in pancreatic carcinoma. Oncogene 2003; 22:3806-12.
17. Tokinaga K, Okuda H, Nomura A, Ashida S, Furihata M, Shuin T. Hypermethylation of the RASSF1A tumor suppressor gene in Japanese clear cell renal cell carcinoma. Oncol Rep 2004; 12:805-10.
18. Dulaimi E, Ibanez de Caceres I, Uzzo R G, Al-Saleem T, Greenberg R E, Polascik T J, et al. Promoter hypermethylation profile of kidney cancer. Clin Cancer Res 2004; 10:3972-9.
19. Yoon J H, Dammann R, Pfeifer G P. Hypermethylation of the CpG island of the RASSF1A gene in ovarian and renal cell carcinomas. Int J Cancer 2001; 94:212-7.
20. Lee M G, Kim H Y, Byun D S, Lee S J, Lee C H, Kim J I, et al. Frequent epigenetic inactivation of RASSF1A in human bladder carcinoma. Cancer Res 2001; 61:6688-92.
21. Chan M W, Chan L W, Tang N L, Lo K W, Tong J H, Chan A W, et al. Frequent hypermethylation of promoter region of RASSF1A in tumor tissues and voided urine of urinary bladder cancer patients. Int J Cancer 2003; 104: 611-6.
22. van Engeland M, Roemen G M, Brink M, Pachen M M, Weijenberg M P, de Bruine A P, et al. K-ras mutations and RASSF1A promoter methylation in colorectal cancer. Oncogene 2002; 21:3792-5.
23. Wagner K J, Cooper W N, Grundy R G, Caldwell G, Jones C, Wadey R B, et al. Frequent RASSF1A tumour suppressor gene promoter methylation in Wilms' tumour and colorectal cancer. Oncogene 2002; 21:7277-82.
24. Xu X L, Yu J, Zhang H Y, Sun M H, Gu J, Du X, et al. Methylation profile of the promoter CpG islands of 31 genes that may contribute to colorectal carcinogenesis. World J Gastroenterol 2004; 10:3441-54.
25. Makarla P B, Saboorian M H, Ashfaq R, Toyooka K O, Toyooka S, Minna J D, et al. Promoter hypermethylation profile of ovarian epithelial neoplasms. Clin Cancer Res 2005; 11:5365-9.
26. Dhillon V S, Aslam M, Husain S A. The contribution of genetic and epigenetic changes in granulosa cell tumors of ovarian origin. Clin Cancer Res 2004; 10:5537-45.
27. Ito M, Ito G, Kondo M, Uchiyama M, Fukui T, Mori S, et al. Frequent inactivation of RASSF1A, BLU, and SEMA3B on 3p21.3 by promoter hypermethylation and allele loss in non-small cell lung cancer. Cancer Lett 2005; 225:131-9.
28. Choi N, Son D S, Song I, Lee H S, Lim Y S, Song M S, et al. RASSF1A is not appropriate as an early detection marker or a prognostic marker for non-small cell lung cancer. Int J Cancer 2005; 115:575-81.

Other preferred tumor suppressor genes showing hypermethylation in tumors are listed in Table III.

TABLE III

Examples of tumor suppressor genes which promoter regions are frequently inactivated by methylation in cancers:

| Tumor suppressor gene | Types of cancer in which the gene may be aberrantly methylated | References |
|---|---|---|
| APC | colorectal, breast, head and neck, esophagus, bladder, prostate, stomach, lung, kidney | (1-13) |
| DAP-kinase | pancreas, stomach, lung, colorectal, breast, cervix, nasopharynx | (9, 10, 14-19) |
| E-cadherin | breast, lung, stomach, colorectal, prostate, bladder, cervix, kidney | (8, 20-27) |
| GSTPI | lung, stomach, bladder, prostate, breast, cervix | (8, 9, 11, 12, 28-31) |
| hMLHI | stomach, colorectal, cervix, liver, esophagus, lung, ovary, prostate | (6, 9, 16, 21, 31-34) |
| MGMT | lung, colorectal, bladder, cervix, breast, esophagus, prostate, nasopharynx, kidney | (8, 11, 13, 15-17, 28, 31, 35, 36) |
| NORE1A | kidney, lung, breast, colon | (37-39) |
| p14 | colorectal, bladder, nasopharynx, kidney, stomach, breast | (11, 13, 16, 19, 40-42) |
| p15 | bladder, nasopharynx, kidney, multiple myeloma, colorectal, lung, ovary, stomach | (7, 11, 19, 27, 43-46) |
| P16INK4a | lung, stomach, bladder, cervix, nasopharynx, breast, prostate, kidney, liver, colorectal, pancreas, leukemia, multiple myeloma, thyroid | (8, 9, 11, 15, 17, 18, 27, 28, 35, 43, 44, 47-49) |
| RARbeta | lung, breast, nasopharynx, prostate, kidney, stomach | (8, 12, 13, 19, 23, 30, 35, 50) |
| SOCS1 | colorectal, leukemia, stomach, ovary, liver, pancreas | (51-57) |
| Rb | retinoblastoma, lung, esophagus, stomach | (58-61) |
| VHL | kidney | (13, 62) |

REFERENCES FOR TABLE III

1. Hiltunen M O, Alhonen L, Koistinaho J, Myohanen S, Paakkonen M, Marin S, et al. Hypermethylation of the APC (adenomatous polyposis coli) gene promoter region in human colorectal carcinoma. Int J Cancer 1997; 70:644-8.
2. Jin Z, Tamura G, Tsuchiya T, Sakata K, Kashiwaba M, Osakabe M, Motoyama T. Adenomatous polyposis coli (APC) gene promoter hypermethylation in primary breast cancers. Br J Cancer 2001; 85:69-73.
3. Safar A M, Spencer H, 3rd, Su X, Coffey M, Cooney C A, Ratnasinghe L D, et al. Methylation profiling of archived non-small cell lung cancer: a promising prognostic system. Clin Cancer Res 2005; 11:4400-5.
4. Kawakami K, Brabender J, Lord R V, Groshen S, Greenwald B D, Krasna M J, et al. Hypermethylated APC DNA in plasma and prognosis of patients with esophageal adenocarcinoma. J Natl Cancer Inst 2000; 92:1805-11.
5. Maruyama R, Toyooka S, Toyooka K O, Harada K, Virmani A K, Zochbauer-Muller S, et al. Aberrant promoter methylation profile of bladder cancer and its relationship to clinicopathological features. Cancer Res 2001; 61:8659-63.
6. Yegnasubramanian S, Kowalski J, Gonzalgo M L, Zahurak M, Piantadosi S, Walsh P C, et al. Hypermethylation of CpG islands in primary and metastatic human prostate cancer. Cancer Res 2004; 64:1975-86.
7. Leung W K, To K F, Chu E S, Chan M W, Bai A H, Ng E K, et al. Potential diagnostic and prognostic values of detecting promoter hypermethylation in the serum of patients with gastric cancer. Br J Cancer 2005; 92:2190-4.
8. Toyooka S, Maruyama R, Toyooka K O, McLerran D, Feng Z, Fukuyama Y, et al. Smoke exposure, histologic type and geography-related differences in the methylation profiles of non-small cell lung cancer. Int J Cancer 2003; 103:153-60.
9. Tamura G. Alterations of tumor suppressor and tumor-related genes in the development and progression of gastric cancer. World J Gastroenterol 2006; 12:192-8.
10. Dulaimi E, Hillinck J, Ibanez de Caceres I, Al-Saleem T, Cairns P. Tumor suppressor gene promoter hypermethylation in serum of breast cancer patients. Clin Cancer Res 2004; 10:6189-93.
11. Gutierrez M I, Siraj A K, Khaled H, Koon N, El-Rifai W, Bhatia K. CpG island methylation in Schistosoma- and non-Schistosoma-associated bladder cancer. Mod Pathol 2004; 17:1268-74.
12. Hoque M O, Feng Q, Toure P, Dem A, Critchlow C W, Hawes S E, et al. Detection of aberrant methylation of four genes in plasma DNA for the detection of breast cancer. J Clin Oncol 2006.
13. Dulaimi E, Ibanez de Caceres I, Uzzo R G, Al-Saleem T, Greenberg R E, Polascik T J, et al. Promoter hypermethylation profile of kidney cancer. Clin Cancer Res 2004; 10:3972-9.
14. Dansranjavin T, Mobius C, Tannapfel A, Bartels M, Wittekind C, Hauss J, Witzigmann, H. E-cadherin and DAP kinase in pancreatic adenocarcinoma and corresponding lymph node metastases. Oncol Rep 2006; 15:1125-31.
15. Fujiwara K, Fujimoto N, Tabata M, Nishii K, Matsuo K, Hotta K, et al. Identification of epigenetic aberrant promoter methylation in serum DNA is useful for early detection of lung cancer. Clin Cancer Res 2005; 11:1219-25.
16. Anacleto C, Rossi B, Lopes A, Soares F A, Rocha J C, Caballero O, et al. Development and application of a multiplex PCR procedure for the detection of DNA methylation in colorectal cancer. Oncol Rep 2005; 13:325-8.
17. Yang H J, Liu V W, Wang Y, Chan K Y, Tsang P C, Khoo U S, et al. Detection of hypermethylated genes in tumor and plasma of cervical cancer patients. Gynecol Oncol 2004; 93:435-40.
18. Tong J H, Tsang R K, Lo K W, Woo J K, Kwong J, Chan M W, et al. Quantitative Epstein-Barr virus DNA analysis and detection of gene promoter hypermethylation in nasopharyngeal (NP) brushing samples from patients with NP carcinoma. Clin Cancer Res 2002; 8:2612-9.
19. Kwong J, Lo K W, To K F, Teo P M, Johnson P J, Huang D P. Promoter hypermethylation of multiple genes in nasopharyngeal carcinoma. Clin Cancer Res 2002; 8:131-7.
20. Sarrio D, Moreno-Bueno G, Hardisson D, Sanchez-Estevez C, Guo M, Herman J G, at al. Epigenetic and genetic alterations of APC and CDH1 genes in lobular breast cancer: relationships with abnormal E-cadherin and catenin expression and microsatellite instability. Int J Cancer 2003; 106:208-15.
21. Fox E J, Leahy D T, Geraghty R, Mulcahy H E, Fennelly D, Hyland J M, et al. Mutually exclusive promoter hypermethylation patterns of hMLH1 and O6-methylguanine DNA methyltransferase in colorectal cancer. J Mol Diagn 2006; 8:68-75.
22. Hiraguri S, Godfrey T, Nakamura H, Graff J, Collins C, Shayesteh L, et al. Mechanisms of inactivation of E-cadherin in breast cancer cell lines. Cancer Res 1998; 58:1972-7.
23. Zochbauer-Muller S, Fong K M, Virmani A K, Geradts J, Gazdar A F, Minna J D. Aberrant promoter methylation of multiple genes in non-small cell lung cancers. Cancer Res 2001; 61:249-55.
24. Li L C, Zhao H, Nakajima K, Oh B R, Ribeiro Filho L A, Carroll P, Dahiya R. Methylation of the E-cadherin gene promoter correlates with progression of prostate cancer. J Urol 2001; 166:705-9.
25. Bornman D M, Mathew S, Alsruhe J, Herman J G, Gabrielson E. Methylation of the E-cadherin gene in bladder neoplasia and in normal urothelial epithelium from elderly individuals. Am J Pathol 2001; 159:831-5.
26. Chen C L, Liu S S, Ip S M, Wong L C, Ng T Y, Ngan H Y. E-cadherin expression is silenced by DNA methylation in cervical cancer cell lines and tumours. Eur J Cancer 2003; 39:517-23.
27. Kawakami T, Okamoto K, Ogawa O, Okada Y. Multipoint methylation and expression analysis of tumor suppressor genes in human renal cancer cells. Urology 2003; 61:226-30.
28. Hoque M O, Topaloglu O, Begum S, Henrique R, Rosenbaum E, Van Criekinge W, et al. Quantitative methylation-specific polymerase chain reaction gene patterns in urine sediment distinguish prostate cancer patients from control subjects. J Clin Oncol 2005; 23:6569-75.
29. Hoque M O, Begum S, Topaloglu O, Chatterjee A, Rosenbaum E, Van Criekinge W, et al. Quantitation of promoter methylation of multiple genes in urine DNA and bladder cancer detection. J Natl Cancer Inst 2006; 98:996-1004.
30. Grover A C, Tangrea M A, Woodson K G, Wallis B S, Hanson J C, Chuaqui R F, et al. Tumor-associated endothelial cells display GSTP1 and RARbeta2 promoter methylation in human prostate cancer. J Transl Med 2006; 4:13.
31. Virmani A K, Muller C, Rathi A, Zoechbauer-Mueller S, Mathis M, Gazdar A F. Aberrant methylation during cervical carcinogenesis. Clin Cancer Res 2001; 7:584-9.
32. Tzao C, Hsu H S, Sun G H, Lai H L, Wang Y C, Tung H J, et al. Promoter methylation of the hMLH1 gene and protein expression of human mutL homolog 1 and human mutS homolog 2 in resected esophageal squamous cell carcinoma. J Thorac Cardiovasc Surg 2005; 130:1371.
33. Hsu H S, Wen C K, Tang Y A, Lin R K, Li W Y, Hsu W H, Wang Y C. Promoter hypermethylation is the predominant mechanism in hMLH1 and hMSH2 deregulation and is a poor prognostic factor in nonsmoking lung cancer. Clin Cancer Res 2005; 11:5410-6.
34. Gifford G, Paul J, Vasey P A, Kaye S B, Brown R. The acquisition of hMLH1 methylation in plasma DNA after chemotherapy predicts poor survival for ovarian cancer patients. Clin Cancer Res 2004; 10:4420-6.

35. Munot K, Bell S M, Lane S, Horgan K, Hanby A M, Speirs V. Pattern of expression of genes linked to epigenetic silencing in human breast cancer. Hum Pathol 2006; 37:989-99.
36. Baumann S, Keller G, Puhringer F, Napieralski R, Feith M, Langer R, et al. The prognostic impact of O6-Methylguanine-DNA Methyltransferase (MGMT) promotor hypermethylation in esophageal adenocarcinoma. Int J Cancer 2006; 119:264-8.
37. Hesson L, Dallol A, Minna J D, Maher E R, Latif F. NORE1A, a homologue of RASSF1A tumour suppressor gene is inactivated in human cancers. Oncogene 2003; 22:947-54.
38. Irimia M, Fraga M F, Sanchez-Cespedes M, Esteller M. CpG island promoter hypermethylation of the Ras-effector gene NORE1A occurs in the context of a wild-type K-ras in lung cancer. Oncogene 2004; 23:8695-9.
39. Hesson L B, Wilson R, Morton D, Adams C, Walker M, Maher E R, Latif F. CpG island promoter hypermethylation of a novel Ras-effector gene RASSF2A is an early event in colon carcinogenesis and correlates inversely with K-ras mutations. Oncogene 2005; 24:3987-94.
40. Sato F, Harpaz N, Shibata D, Xu Y, Yin J, Mori Y, et al. Hypermethylation of the p14(ARF) gene in ulcerative colitis-associated colorectal carcinogenesis. Cancer Res 2002; 62:1148-51.
41. Iida S, Akiyama Y, Nakajima T, Ichikawa W, Nihei Z, Sugihara K, Yuasa Y. Alterations and hypermethylation of the p14(ARF) gene in gastric cancer. Int J Cancer 2000; 87:654-8.
42. Dominguez G, Silva J, Garcia J M, Silva J M, Rodriguez R, Munoz C, et al. Prevalence of aberrant methylation of p14ARF over p16INK4a in some human primary tumors. Mutat Res 2003; 530:9-17.
43. Chen W, Wu Y, Zhu J, Liu J, Tan S, Xia C. Methylation of p16 and p15 genes in multiple myeloma. Chin Med Sci J 2002; 17:101-5.
44. Yang B, Guo M, Herman J G, Clark D P. Aberrant promoter methylation profiles of tumor suppressor genes in hepatocellular carcinoma. Am J Pathol 2003; 163:1101-7.
45. Kurakawa E, Shimamoto T, Utsumi K, Hirano T, Kato H, Ohyashiki K. Hypermethylation of p16(INK4a) and p15 (INK4b) genes in non-small cell lung cancer. Int J Oncol 2001; 19:277-81.
46. Liu Z, Wang L E, Wang L, Lu K H, Mills G B, Bondy M L, Wei Q. Methylation and messenger RNA expression of p15INK4b but not p16INK4a are independent risk factors for ovarian cancer. Clin Cancer Res 2005; 11:4968-76.
47. Wenming C, Jiazhi Z, Shuzhen T, Bai X, Jingzhong L. Inactivation of p16 gene in leukemia. Chin Med Sci J 1999; 14:206-10.
48. Boltze C, Zack S, Quednow C, Bettge S, Roessner A, Schneider-Stock R. Hypermethylation of the CDKN2/p16INK4A promotor in thyroid carcinogenesis. Pathol Res Pract 2003; 199:399-404.
49. Lin S Y, Yeh K T, Chen W T, Chen H C, Chen S T, Chiou H Y, Chang J G. Promoter CpG methylation of tumor suppressor genes in colorectal cancer and its relationship to clinical features. Oncol Rep 2004; 11:341-8.
50. Ikoma H, Ichikawa D, Koike H, Ikoma D, Tani N, Okamoto K, et al. Correlation between serum DNA methylation and prognosis in gastric cancer patients. Anticancer Res 2006; 26:2313-6.
51. Fujitake S, Hibi K, Okochi O, Kodera Y, Ito K, Akiyama S, Nakao A. Aberrant methylation of SOCS-1 was observed in younger colorectal cancer patients. J Gastroenterol 2004; 39:120-4.
52. Ekmekci C G, Gutierrez M I, Siraj A K, Ozbek U, Bhatia K. Aberrant methylation of multiple tumor suppressor genes in acute myeloid leukemia. Am J Hematol 2004; 77:233-40.
53. Oshimo Y, Kuraoka K, Nakayama H, Kitadai Y, Yoshida K, Chayama K, Yasui W. Epigenetic inactivation of SOCS-1 by CpG island hypermethylation in human gastric carcinoma. Int J Cancer 2004; 112:1003-9.
54. Sutherland K D, Lindeman G J, Choong D Y, Wittlin S, Brentzell L, Phillips W, et al. Differential hypermethylation of SOCS genes in ovarian and breast carcinomas. Oncogene 2004; 23:7726-33.
55. Komazaki T, Nagai H, Emi M, Terada Y, Yabe A, Jin E, et al. Hypermethylation-associated inactivation of the SOCS-1 gene, a JAX/STAT inhibitor, in human pancreatic cancers. Jpn J Clin Oncol 2004; 34:191-4.
56. Yoshikawa H, Matsubara K, Qian G S, Jackson P, Groopman J D, Manning J E, et al. SOCS-1, a negative regulator of the JAK/STAT pathway, is silenced by methylation in human hepatocellular carcinoma and shows growth-suppression activity. Nat Genet 2001; 28:29-35.
57. Chen C Y, Tsay W, Tang J L, Shen H L, Lin S W, Huang S Y, et al. SOCS1 methylation in patients with newly diagnosed acute myeloid leukemia. Genes Chromosomes Cancer 2003; 37:300-5.
58. Ye Y, Su C, Wang D, Liu S, Liu Y, Liu B, et al. Relationship between tumor suppressor gene p16 and Rb and early diagnosis of lung cancers. Zhonghua Wai Ke Za Zhi 2000; 38:537-41, 30.
59. Stirzaker C, Millar D S, Paul C L, Warnecke P M, Harrison J, Vincent P C, et al. Extensive DNA methylation spanning the Rb promoter in retinoblastoma tumors. Cancer Res 1997; 57:2229-37.
60. Esteller M. Epigenetic lesions causing genetic lesions in human cancer: promoter hypermethylation of DNA repair genes. Eur J Cancer 2000; 36:2294-300.
61. Li H, Lu S, Fong L. Study on the states of methylation of Rb gene promoter in human esophageal cancer and effect of NMBzA on Rb gene promoter in monkey esophageal epithelium. Zhonghua Zhong Liu Za Zhi 1998; 20:412-4.
62. Banks R E, Tirukonda P, Taylor C, Hornigold N, Astuti D, Cohen D, et al. Genetic and epigenetic analysis of von Hippel-Lindau (VHL) gene alterations and relationship with clinical variables in sporadic renal cancer. Cancer Res 2006; 66:2000-11.

In accordance with the method of the present invention a sample is taken or obtained from the patient. Suitable samples include blood, plasma, serum, saliva and urine. Samples to be used in accordance with the present invention include whole blood, plasma or serum. Methods for preparing serum or plasma from whole blood are well known among those of skill in the art. For example, blood can be placed in a tube containing EDTA or a specialised commercial product such as Vacutainer SST (Becton Dickenson, Franklin Lake, N.J.) to prevent blood clotting, and plasma can then be obtained from whole blood through centrifugation. Serum may be obtained with or without centrifugation following blood clotting. If centrifugation is used then it is typically, though not exclusively conducted at an appropriate speed, for example, 1500-3000×g. Plasma or serum may be subjected to additional centrifugation steps before being transferred to a fresh tube for DNA extraction.

Preferably, DNA is extracted from the sample using a suitable DNA extraction technique. Extraction of DNA is a matter of routine for one of skill in the art. There are numerous known methods for extracting DNA from a biological sample including blood. General methods of DNA preparation, for example described by Sambrook and Russell, Molecular Cloning a Laboratory Manual, 3$^{rd}$ Edition (2001) can be followed. Various commercially available reagents or kits may also be used to obtain DNA from a blood sample.

In accordance with the invention, the DNA containing sample is incubated with one or more restriction enzyme(s) which preferentially cut unmethylated DNA under conditions such that where two or more restriction enzyme sites are present in the target sequence in the unmethylated state, the restriction enzyme(s) can cut the target sequence at at least one such site. In accordance with an alternative aspect of the invention, a DNA sample is incubated with one or more restriction enzymes which only cut methylated DNA under conditions such that where two or more restriction enzyme sites are present in the methylated state, the restriction enzyme(s) can cut the target sequence at at least one such site.

Preferably samples are incubated under conditions to allow complete digestion. This may be achieved, for example by increasing the incubation times and/or increasing the quantity of the enzyme used. Typically, the sample will be incubated with 100 active units of methylation-sensitive restriction enzyme for a period of up to 16 hours. It is a matter of routine for one of skill in the art to establish suitable conditions based on the quantity of enzyme used.

After incubation, uncut target sequences are detected. Preferably, these sequences are detected by amplification, for example using the polymerase chain reaction (PCR).

DNA primers are designed to amplify a sequence containing at least two methylation-sensitive restriction enzyme sites. Such sequences can be identified by looking at DNA methylation markers and identifying restriction enzyme sites within those markets which are recognised by methylation-sensitive enzymes. For example using the recognition sequences for the methylation-sensitive enzymes identified in Table I, suitable target sequences can be identified in the methylation markers listed in Table III.

Using RASSF1A as an example, the target sequence may comprise part or all of the promoter sequence and/or exon 1 of the RASSF1A gene. The sequence for the promoter and exon 1 is set out in FIG. 6 (SEQ NO: 1). In a preferred embodiment the target sequence for detection is that highlighted in bold in FIG. 6 (residues 1142 to 1269 of SEQ ID NO: 1). In a more preferred embodiment residues 1142 to 1269 of SEQ ID NO: 1 are amplified using (a) a primer comprising or consisting of the sequence shown in SEQ ID NO: 2 and (b) a primer comprising or consisting of the sequence shown in SEQ ID NO: 3. In another more preferred embodiment residues 1142 to 1269 of SEQ ID NO: 1 are detected using a detectably-labelled probe comprising the sequence shown in SEQ ID NO: 4. In an even more preferred embodiment residues 1142 to 1269 of SEQ ID NO: 1 are detected using a detectably-labelled probe comprising the sequence shown in SEQ ID NO: 4 and no additional nucleotides.

When using methylation-sensitive enzymes, altered quantities of the target sequence will be detected depending on the methylation status of the target sequence in a particular individual. In the preferred aspect of the present invention using methylation-sensitive restriction enzymes which preferentially cut unmethylated DNA, the target sequence will not be detected in the unmethylated state, for example in a healthy individual. However, where the target sequence is methylated, for example in a selected sample from a cancer patient, the target sequence is not cut by the restriction enzyme and the target sequence can thus be detected by PCR.

Thus, the method can be used to determine the methylation status of the target sequence and provide an indication of the cancer status of the individual.

The methods of the present invention may additionally include quantifying or detecting a control sequence. The control sequence is selected which does not show aberrant methylation patterns in cancer. In accordance with a preferred aspect of the present invention, the control sequence is selected to contain at least two methylation-sensitive restriction enzyme recognition sites. Preferably, the control sequence is selected to contain the same number of methylation-sensitive restriction enzyme recognition sites as the DNA sequence of interest. Typically the presence or absence of such control sequences is detected by amplification by the polymerase chain reaction after digestion with the methylation-sensitive restriction enzyme(s). Such control sequences can be used to assess the extent of digestion with the one or more methylation-sensitive restriction enzymes. For example, if after digestion with the methylation-sensitive restriction enzyme(s) control sequences are detectable, this would indicate that the digestion is not complete and the methods can be repeated to ensure that complete digestion has occurred. Preferably the control sequence is selected to contain the same methylation-sensitive restriction enzyme sites that are present in the target sequence. In a preferred embodiment the control sequence is β-actin. In a more preferred embodiment a target sequence in the β-actin is amplified using (a) a primer comprising or consisting of the sequence shown in SEQ ID NO: 5 and (b) a primer comprising or consisting of the sequence shown in SEQ ID NO: 6. In an even more preferred embodiment the target sequence in β-actin (which is amplified using primers comprising SEQ NOs: 5 and 6) is detected using a detectably-labelled probe comprising the sequence shown in SEQ ID NO: 7. In an even more preferred embodiment the target sequence is detected using a detectably-labelled probe comprising the sequence shown in SEQ ID NO: 7 and no additional nucleotides.

The present methods can be used to assess the tumor status of an individual. The methods can be used, for example, in the diagnosis and/or prognosis of cancer. The methods can also be used to monitor the progress of cancer, for example, during treatment. The methods can also be used to monitor changes in the levels of methylation over time, for example to assess the susceptibility of an individual to cancer, and the progression of the disease. The methods can also be used to predict the outcome of disease or the likelihood of success of treatment.

In a preferred aspect of the present invention the target sequence is RASSF1A and is used in the diagnosis of cancer. For example, RASSF1A methylation can be used to detect and monitor hepatocellular or nasopharyngeal carcinoma. The method is particularly useful in monitoring the susceptibility of a hepatitis B carrier or a hepatitis C carrier to hepatocellular carcinoma.

In another aspect of the invention, there is provided probes and primers for use in the method of the invention. Firstly, there is provided a set of primers or a detectably-labelled probe for the detection or monitoring of cancer in a biological sample selected from blood, plasma, serum, saliva, urine from an individual. The set of primers comprises or consists of (a) a primer comprising or consisting of the sequence shown in SEQ ID NO: 2 and (b) a primer comprising or consisting of the sequence shown in SEQ ID NO: 3. The set of primers is capable of amplifying residues 1142 to 1269 of SEQ ID NO: 1 (i.e. part of the promoter and first exon of the RASSF1A gene). The detectably-labelled probe comprises the sequence shown in SEQ ID NO: 4 and is capable of detecting residues 1142 to 1269 of SEQ ID NO: 1. The detectably-labelled probe preferably comprises the sequence shown in SEQ ID NO: 4 and no additional nucleotides. The detectably-labelled probe is most preferably the probe used in the Examples.

Secondly, there is provided a set of primers and a detectably-labelled probe for use as a control during the detection or monitoring of cancer in a biological sample selected from blood, plasma, serum, saliva, urine from an individual. The set of primers comprises or consists of (a) a primer comprising or consisting of the sequence shown in SEQ ID NO: 5 and (b) a primer comprising or consisting of the sequence shown in SEQ ID NO: 6. The set of primers is capable of amplifying a target sequence in β-actin. The detectably-labelled probe comprises the sequence shown in SEQ ED NO: 7 and is capable of detecting the target sequence in β-actin that is amplified by the printers comprising SEQ ID NOs: 5 and 6. The detectably-labelled probe preferably comprises the sequence shown in SEQ ID NO: 7 and no additional nucleotides. The detectably-labelled control probe is most preferably the control probe used in the Examples.

The probes are detectably-labelled. The detectable label allows the presence or absence of the hybridization product formed by specific hybridization between the probe and the target sequence to be determined. Any label can be used. Suitable labels include, but are not limited to, fluorescent molecules, radioisotopes, e.g. $^{125}$I, $^{35}$S, enzymes, antibodies and linkers such as biotin.

In another aspect, there is provided kits for use in the method of invention. Firstly, there is provided a kit for the detection or monitoring of cancer in a biological sample selected from blood, plasma, serum, saliva, urine from an individual. The kit comprises (a) a primer comprising or consisting of the sequence shown in SEQ NO: 2, (b) a primer comprising or consisting of the sequence shown in SEQ ID NO: 3 and (c) a detectably-labelled probe comprising the sequence shown in SEQ ID NO: 4 and optionally no additional nucleotides. The kit is capable of amplifying and detecting residues 1142 to 1269 of SEQ ID NO: 1.

Secondly, there is provided a kit for use as a control during the detection or monitoring of cancer in a biological sample selected from blood, plasma, serum, saliva, urine from an individual. The kit comprises (a) a primer comprising or consisting of the sequence shown in SEQ ID NO: 5, (b) a primer comprising or consisting of the sequence shown in SEQ ID NO: 6 and (c) a detectably-labelled probe comprising the sequence shown in SEQ ID NO: 7 and optionally no additional nucleotides. The kit is capable of amplifying and detecting a target sequence in β-actin.

The kits of the invention may additionally comprise one or more other reagents or instruments which enable the method of the invention as described above to be carried out. Such reagents or instruments include one or more of the following: suitable buffer(s) (aqueous solutions), PCR reagents, fluorescent markers and/or reagents, means to obtain a sample from individual subject (such as a vessel or an instrument comprising a needle) or a support comprising wells on which reactions can be done. Reagants may be present in the kit in a dry state such that the fluid sample resuspends the reagents. The kit may, optionally, comprise instructions to enable the kit to be used in the method of the invention.

The invention is hereinafter described in more detail by reference to the Examples below.

EXAMPLES

Sixty-three hepatocellular carcinoma (HCC) patients, as well as two groups of controls, were recruited. The first control group consisted of 15 healthy control subjects without chronic hepatitis B infection. The second control group consisted of chronic hepatitis B carriers. For each HCC patient, one sex- and age-matched chronic hepatitis B carrier was recruited as a control. Chronic hepatitis B carriers had increased risk of developing HCC and, thus, would be the target group for HCC screening. Four milliliters of venous blood were collected from each study subject into EDTA-containing tubes. Blood samples were centrifuged at 1,600 g for 10 min and the supernatant was re-centrifuged at 16,000 g for 10 min. DNA was then extracted from 800 μL of plasma using the QIAamp mini kit (Qiagen, Hilden, Germany) and eluted with 50 μL of $H_2O$. Thirty-five microliters of plasma DNA were digested with 100 U of BstUI enzyme, in 1× digestion buffer at 60° C. for 16 hours.

The concentration of plasma RASSF1A sequence was determined by real-time PCR using the primers 5'AGCCTGAGCTCATTGAGCTG3' (SEQ ID NO: 2) and 5'ACCAGCTGCCGTGTGG3' (SEQ ID NO: 3), and the probe 5'FAM-CCAACGCGCTGCGCAT(MGB)3' (SEQ ID NO: 4). Each reaction contains 1× TaqMan Universal PCR Master Mix (Applied Biosystems, Foster City), 300 nM each of the primers and 85 nM of probes. 7.15 microliters of enzyme-digested plasma DNA mixture (equivalent to 5 μL of undigested plasma DNA) were used as the template for each PCR reaction. The thermal profile was 50° C. for 2 minutes, 95° C. for 10 minutes, 50 cycles of 95° C. for 15 seconds and 60° C. for 1 minute. All reactions were run in duplicate and the mean quantity was taken. The RASSF1A amplicon embraced 5 restriction sites of BstUI.

To ensure the completeness of the restriction enzyme digestion, real-time PCR targeting the β-actin gene was performed for each enzyme digested samples using the primers 5' GCGCCGTTCCGAAAGTT3' (SEQ ID NO: 5) and 5'CGGCGGATCGGCAAA3' (SEQ ID NO: 6), and the probe 5'FAM-ACCGCCGAGACCGCGTC(MGB)3' (SEQ ID NO: 7). By bisulfite sequencing, the β-actin gene promoter was shown to be completely unmethylated in blood cells and HCC tissues. The β-actin amplicon is of similar size of the RASSF1A amplicon and contains identical number of BstUI enzyme restriction sites.

To investigate if the enzyme digestion efficiencies for unmethylated RASSF1A and β-actin sequences were similar, aliquots of 1 μg of buffy coat were digested with 100 U of BstUI enzyme for different time intervals (15 minutes, 30 minutes, 45 minutes, 60 minutes, 90 minutes, 120 minutes, 3 hours, 4 hours, 5 hours, 6 hours, 12 hours and 16 hours). The concentrations of RASSF1A and β-actin sequences were measured in each sample after the enzyme digestion. As shown in FIG. 1, the concentrations of RASSF1A and β-actin sequences in these buffy coat DNA showed a positive correlation (r=0.986, P<0.0001, Pearson correlation). As the enzyme digestion efficiencies for unmethylated RASSF1A and β-actin sequences are similar, the completeness of the digestion of unmethylated RASSF1A sequence should be reflected by the absence of β-actin sequence in the digested plasma DNA sample. Therefore, all samples with positive β-actin signal were subject to further enzyme digestion until no β-actin sequence was detectable in the digested plasma DNA sample.

Figure 2:
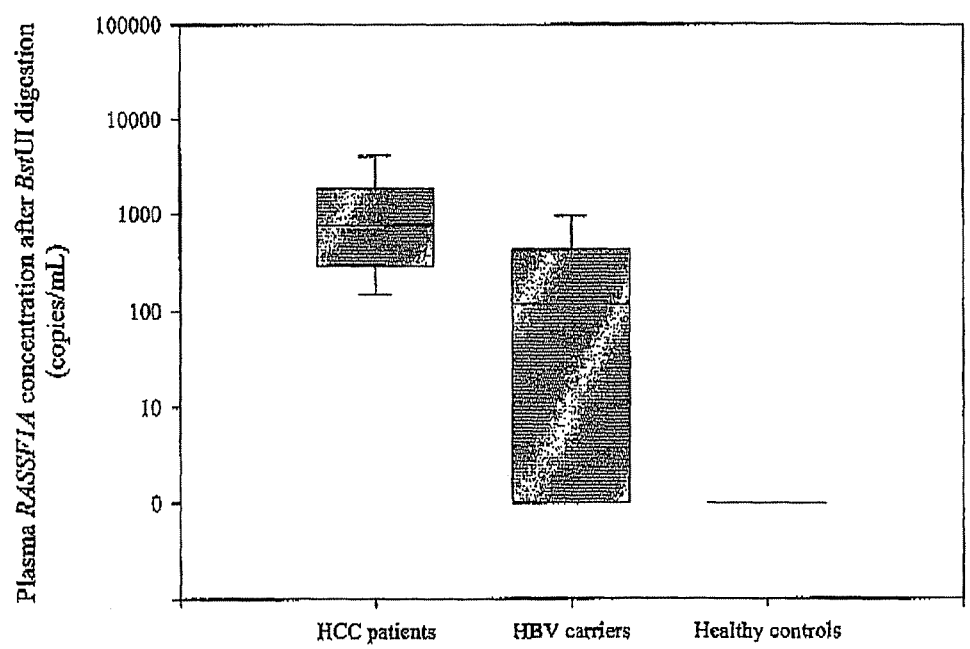
FIG. 2: changes of plasma methylated RASSF1A levels after surgical resection of hepatocellular carcinoma (HCC).

After BstUI enzyme digestion, RASSF1A sequences were detected in the plasma of 59 (93%) of the 63 HCC patients and 37 (58%) of the 63 matched chronic hepatitis B carriers (HBV carriers). These results are shown in FIG. 2. The median plasma RASSF1A concentrations of the HCC patients and chronic hepatitis B carriers were 770 copies/mL and 118 copies/mL, respectively. In contrast, RASSF1A was not detectable in the plasma of any of the 15 healthy subjects.

Figure 3:
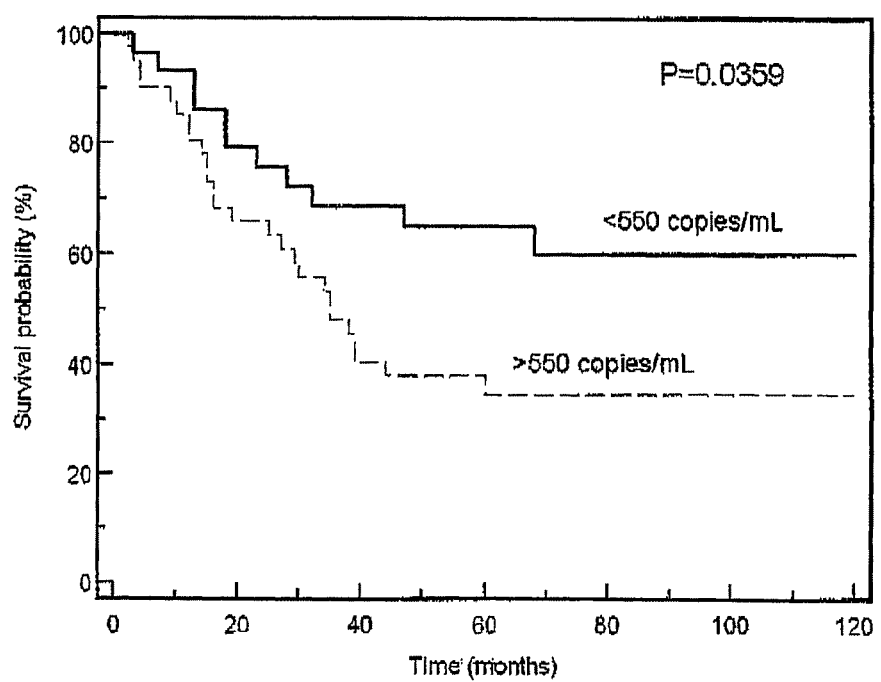
FIG. 3: methylated RASSF1A sequence concentration in plasma prior to surgical resection is predictive of patient survival after surgical resection.

FIG. 3 demonstrates that the survival probabilities of HCC patients with preoperative plasma RASSF1A concentration of less than 550 copies/mL were better than those with levels higher than 550 copies/mL (p=0.0359, Kaplan-Meier survival analysis).

Figure 4:
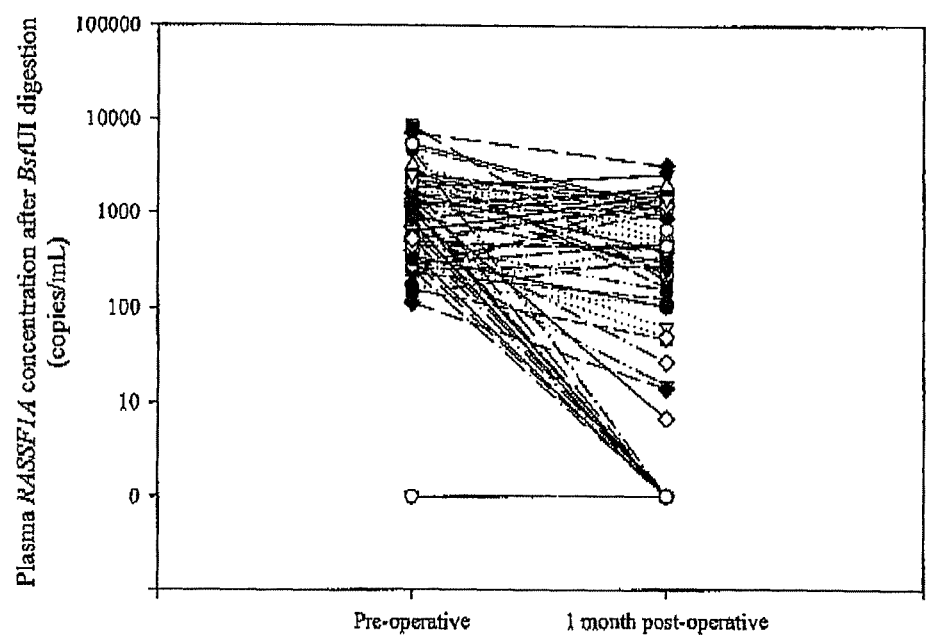
FIG. 4: methylated RASSF1A sequence concentration in plasma post-surgical resection is predictive of patients survival after surgical resection.

Blood samples were collected from the HCC patients at 1 month after the surgical resection of the tumor. In the 59 patients with detectable plasma RASSF1A before tumor resection, 45 of them (76%) showed a reduction in the concentration after the operation. These results are shown in FIG. 4. Among these 45 patients, 13 of them had undetectable RASSF1A after the resection of tumor. The median RASSF1A concentration dropped from 770 copies/mL to 250 copies/mL (p<0.0001, Wilcoxon test).

Figure 5:
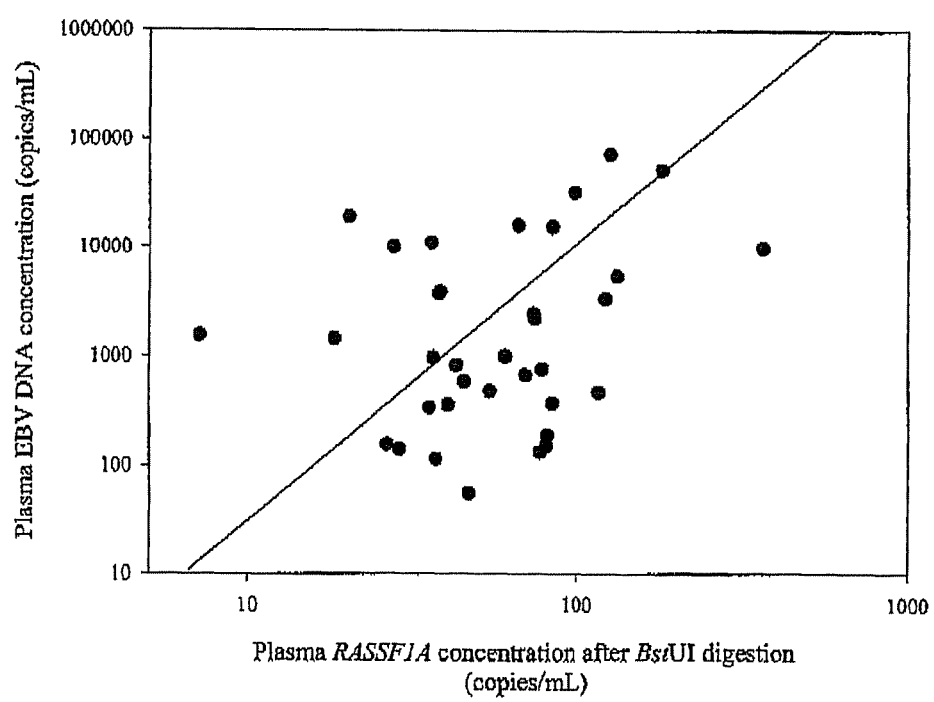
FIG. 5: concentration of methylated RASSF1A detected in the plasma of nasopharangeal carcinoma (NPC) patients correlated with Epstein-Barr virus (EBV) DNA concentration.

To further investigate if the quantitative analysis of plasma RASSF1A after methylation-sensitive restriction enzyme digestion is a generic marker for cancers with aberrant methylation of RASSF1A, 67 nasopharyngeal carcinoma (NPC) patients were recruited for the study of the correlation of the plasma concentrations of enzyme-digestion-resistant RASSF1A and Epstein-Barr virus (EBV) DNA. Plasma EBV DNA is an established marker for NPC and has been shown to reflect tumor load (Lo Y M D, Chan L Y, Lo K W, Leung S F, Zhang J, Chan A T, Lee J C, Hjelm N M, Johnson P J, Huang D P. Quantitative analysis of cell-free Epstein-Barr virus DNA in plasma of patients with nasopharyngeal carcinoma. Cancer Res 1999; 59:1188-91). The results are shown in FIG. 5. EBV DNA and enzyme-digestion-resistant RASSF1A sequence were detectable in the plasma of 65 (94%) and 37 (54%) patients, respectively. In the patients with detectable enzyme-digestion-resistant RASSF1A and EBV DNA, the plasma concentrations of the two DNA sequences showed a positive correlation (r=0.343, p=0.037, Spearman correlation).

The invention claimed is:

1. A method for detection, prognostication, or monitoring of nasopharyngeal cancer using a biological sample from an individual, the method comprising:
   (a) obtaining DNA from the biological sample, wherein the biological sample is selected from the group consisting of blood, plasma, serum, saliva, and urine;
   (b) digesting the DNA with one or more methylation-sensitive restriction enzymes, wherein the one or more methylation-sensitive restriction enzymes preferentially cleave DNA sequences when present in an unmethylated state than in a methylated state;
   (c) determining a level of target sequence in the DNA digested in (b), wherein the target sequence comprises promoter sequence of RASSF1A and at least two methylation-sensitive restriction enzyme recognition sites; and
   (d) detecting, prognosticating, or monitoring nasopharyngeal cancer based on the level of the target sequence determined in (c).

2. The method according to claim 1, wherein (c) comprises using real-time quantitative polymerase chain reaction (Q-PCR) to generate a PCR amplicon, and wherein the PCR amplicon comprises at least two recognition sites for the one or more methylation-sensitive restriction enzymes used in (b).

3. The method according to claim 1, wherein (c) comprises using polymerase chain reaction (PCR) to generate a PCR amplicon, and wherein the PCR amplicon comprises at least two recognition sites for the one or more methylation-sensitive restriction enzymes used in (b).

4. The method according to claim 1, wherein the target sequence in (c) further comprises at least a portion of a second gene which demonstrates an aberrant DNA methylation pattern in cancer.

5. The method according to claim 1, wherein the target sequence further comprises exon 1 of RASSF1A.

6. The method according to claim 1, wherein the target sequence comprises residues 1142 to 1269 of SEQ ID NO: 1.

7. The method according to claim 6, further comprising amplifying the target sequence using a primer comprising SEQ ID NO: 2 and a primer comprising SEQ ID NO: 3; and/or detecting the target sequence using a detectably-labelled probe comprising SEQ ID NO: 4.

8. The method according to claim 4, wherein the second gene is selected from the group consisting of APC, DAP-kinase, E-cadherin, GSTPI, hMLH1, MGMT, NORE1A, p14, p15, P16INK4a, RARbeta, SOCS1, Rb, and VHL.

9. The method according to claim 1, wherein following (b), each DNA from the biological sample is cleaved by at least one methylation-sensitive restriction enzyme when present in an unmethylated state.

10. The method according to claim 1, wherein in (b) the DNA is treated under conditions sufficient to allow digestion of the DNA by (i) increasing a quantity of methylation-sensitive restriction enzyme in a composition comprising the DNA, and/or (ii) extending an incubation time of a composition comprising the DNA.

11. The method according to claim 1, further comprising using the level of the target sequence to: diagnose cancer in the individual; predict susceptibility to cancer of the individual; assess stage of cancer in the individual; predict likelihood of overall survival for the individual; predict likelihood of recurrence of cancer for the individual; or assess treatment effectiveness with respect to cancer for the individual.

12. The method according to claim 11, further comprising quantifying a trend of the level of the target sequence over a time course of treatment, monitoring, or post-treatment.

13. The method according to claim 1, further comprising quantifying or detecting a control DNA sequence from the biological sample that has been digested with the one or more methylation-sensitive restriction enzymes, wherein the control DNA sequence does not demonstrate an aberrant DNA methylation pattern in cancer.

14. The method according to claim 13, wherein the control DNA sequence comprises at least two methylation-sensitive restriction enzyme recognition sites.

15. The method according to claim 14, wherein the control DNA sequence and the target sequence have a same number of methylation-sensitive restriction enzyme recognition sites.

16. The method according to claim 13, wherein the control DNA sequence encodes for β-actin.

17. The method according to claim 16, further comprising subjecting the control DNA sequence to amplification using a primer comprising SEQ ID NO: 5 and a primer comprising SEQ ID NO: 6.

18. The method according to claim 17, further comprising detecting the target sequence using a detectably-labelled probe comprising SEQ ID NO: 7.

19. The method according to claim 13, further comprising assessing an extent or completeness of enzyme digestion.

20. The method according to claim 1, wherein the target sequence comprises a second tumor suppressor gene.

* * * * *

SEQUENCE LISTING

<160> NUMBER OF SEQ ID NOS: 7

<210> SEQ ID NO 1
<211> LENGTH: 1381
<212> TYPE: DNA
<213> ORGANISM: Homo sapiens

<400> SEQUENCE: 1

```
cctagatccc agaaatctgg gagcggctgg agcgagaaaa cagaggcaag tggcaggcaa      60
ttgccaagca ccagctccag catgtgttca gcccctcaga gcaggacctg cggctgcagg     120
cgcgaaggta aggcctgtgg aaatggcagg gagggtggag gggatgcagg aggcatggat     180
gtgggtgggg tgccccacc ttccagggcc agtcagacct tcctgacttt cccccaggtg      240
ggctgagacc tacaggctgg atgtgctaga ggcagtggct ccagagcggc cccgctgtgc     300
ttactgcagt gcagaggctt ctaagcgctg ctcacgatgc cagaatgagt ggtattgctg     360
caggtgaggg tatcctagaa ccttggacct ctaagcccta ctcccacatc ccccacatgc     420
attgccatcc tcaataccca cctgcctgca gggagtgcca agtcaagcac tgggaaaagc     480
atggaaagac ttgtgtcctg gcagcccagg gtgacagagc caaatgaggg ctgcagttgc     540
tgagggccga ccacccatgc caagggaatc cacccagaat gcaccctga acctcaagat      600 cacggtccag cctctgccgg agcccagtc tccgcagtgg agagcagagc gggcggtaaa      660
gctgctgacc gatctccctc ctcctcaccc caagtgaagg ctcgagactt cctgccccac     720
ccagtgggta ggccaagtgt gttgcttcag caaaccggac caggagggcc agggccggat     780 gtgggaccc tcttcctcta gcacagtaaa gctggcctcc agaaacacgg gtatctccgc     840
gtggtgcttt gcggtcgccg tcgttgtggc cgtccggggt ggggtgtgag gaggggacga     900
aggagggaag gaagggcaag gcgggggggg ctctgcgaga gcgcgcccag ccccgccttc     960
gggccccaca gtccctgcac ccaggtttcc attgcgcggc tctcctcagc tccttcccgc    1020
cgcccagtct ggatcctggg ggaggcgctg aagtcggggc ccgccctgtg gccccgcccg    1080
gcccgcgctt gctagcgccc aaagccagcg aagcacgggc ccaaccgggc catgtcgggg    1140
gagcctgagc tcattgagct gcgggagctg gcacccgctg ggcgcgctgg gaagggccgc    1200
```

```
acccggctgg agcgtgccaa cgcgctgcgc atcgcgcggg gcaccgcgtg caacccaca    1260 cggcagctgg tccctggccg tggccaccgc ttccagcccg cggggcccgc cacgcacacg    1320
tggtgcgacc tctgtggcga cttcatctgg ggcgtcgtgc gcaaaggcct gcagtgcgcg    1380
c                                                                    1381

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
agcctgagct cattgagctg                                                  20

<210> SEQ ID NO 3
<211> LENGTH: 16
<212> TYPE: DNA
<213> ORGANISM: Artificial
<220> FEATURE:
<223> OTHER INFORMATION: Primer

<400> SEQUENCE: 3
accagctgcc gtgtgg                                                      16

<210> SEQ ID NO 4
<211> LENGTH: 16
<212> TYPE: DNA
<213> ORGANISM: Artificial
<220> FEATURE:
<223> OTHER INFORMATION: Probe

<400> SEQUENCE: 4
ccaacgcgct gcgcat                                                      16

<210> SEQ ID NO 5
<211> LENGTH: 17
<212> TYPE: DNA
<213> ORGANISM: Artificial
<220> FEATURE:
<223> OTHER INFORMATION: Primer

<400> SEQUENCE: 5
gcgccgttcc gaaagtt                                                     17

<210> SEQ ID NO 6
<211> LENGTH: 15
<212> TYPE: DNA
<213> ORGANISM: Artificial
<220> FEATURE:
<223> OTHER INFORMATION: Primer

<400> SEQUENCE: 6
cggcggatcg gcaaa                                                       15

<210> SEQ ID NO 7
<211> LENGTH: 17
<212> TYPE: DNA
<213> ORGANISM: Artificial
```

```
<220> FEATURE:
<223> OTHER INFORMATION: Probe

<400> SEQUENCE: 7
accgccgaga ccgcgtc                                                    17
```